(12) United States Patent
Hirayama et al.

(10) Patent No.: US 9,322,834 B2
(45) Date of Patent: Apr. 26, 2016

(54) SAMPLE ANALYZER, BLOOD ANALYZER AND DISPLAYING METHOD

(75) Inventors: Hideki Hirayama, Akashi (JP); Yoichi Nakamura, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 1476 days.

(21) Appl. No.: 12/154,773

(22) Filed: May 27, 2008

(65) Prior Publication Data

US 2009/0006003 A1 Jan. 1, 2009

(30) Foreign Application Priority Data

May 30, 2007 (JP) .................................. 2007-143435
Jun. 28, 2007 (JP) .................................. 2007-170008

(51) Int. Cl.
| | | |
|---|---|---|
| A61B 5/00 | (2006.01) | |
| G01N 35/00 | (2006.01) | |
| G01N 15/10 | (2006.01) | |
| G01N 15/00 | (2006.01) | |
| G01N 15/14 | (2006.01) | |

(52) U.S. Cl.
CPC ...... *G01N 35/00584* (2013.01); *G01N 15/1012* (2013.01); *G01N 2015/008* (2013.01); *G01N 2015/0065* (2013.01); *G01N 2015/0073* (2013.01); *G01N 2015/0084* (2013.01); *G01N 2015/1486* (2013.01)

(58) Field of Classification Search
CPC .............................................. G01N 2015/1486
USPC ........... 600/368; 422/44; 702/21; 436/63, 70; 345/418, 581, 589, 593, 594; 382/133, 382/134
See application file for complete search history.

(56) References Cited

U.S. PATENT DOCUMENTS

| | | | | |
|---|---|---|---|---|
| 5,541,064 | A  * | 7/1996 | Bacus et al. | 435/6.12 |
| 6,246,786 | B1 * | 6/2001 | Nishikiori et al. | 382/134 |
| 6,391,263 | B1 * | 5/2002 | Mishima et al. | 422/67 |
| 7,996,188 | B2 * | 8/2011 | Olson et al. | 702/189 |
| 8,017,078 | B2 * | 9/2011 | Linssen et al. | 422/82.01 |

(Continued)

FOREIGN PATENT DOCUMENTS

| | | |
|---|---|---|
| CN | 1880942 A | 12/2006 |
| EP | 1033573 A2 | 9/2000 |

(Continued)

OTHER PUBLICATIONS

Office Action from counterpart Chinese Application No. 200810111351.4, dated Oct. 12, 2010, 4 pages.

*Primary Examiner* — Christian Jang
(74) *Attorney, Agent, or Firm* — Brinks Gilson & Lione

(57) ABSTRACT

The present invention is to present a sample analyzer which is capable of displaying a particle distribution map of a measured sample and a reference particle distribution map so as to be visually compared without reducing a display area for displaying information other than the particle distribution map. The blood analyzer 1 comprises: a display 302; a measurement unit 2 for measuring a blood sample; and a controller 301 being configured to 1) generate a particle distribution map representing a distribution of the particles contained in the blood sample, based on measurement data obtained by the measurement unit 2; and 2) control the display 302 so as to display the particle distribution map of the blood sample at a predetermined display position and to display a reference particle distribution map at the predetermined display position so as to be visually compared with the particle distribution map of the blood sample.

19 Claims, 25 Drawing Sheets

(56) References Cited

U.S. PATENT DOCUMENTS

| | | | |
|---|---|---|---|
| 2001/0037366 A1* | 11/2001 | Webb et al. | 709/204 |
| 2002/0022772 A1* | 2/2002 | Dodds | 600/300 |
| 2004/0254479 A1* | 12/2004 | Fralick et al. | 600/477 |
| 2006/0004530 A1* | 1/2006 | Miyamoto et al. | 702/30 |
| 2006/0111634 A1* | 5/2006 | Wu | 600/443 |
| 2006/0209061 A1* | 9/2006 | Burch et al. | 345/419 |
| 2007/0179715 A1 | 8/2007 | Ariyoshi | |
| 2007/0247463 A1 | 10/2007 | Qian et al. | |
| 2009/0317860 A1 | 12/2009 | Kawate | |

FOREIGN PATENT DOCUMENTS

| | | |
|---|---|---|
| JP | 10-019761 A | 1/1998 |
| JP | 10-090156 A | 4/1998 |
| JP | 2000-310642 A | 11/2000 |
| JP | 2005-537781 A | 12/2005 |
| JP | 2006-234829 A | 9/2006 |
| JP | 2007-078508 A | 3/2007 |
| JP | 2009-534663 A | 9/2009 |
| WO | WO 03/069421 A2 | 8/2003 |

\* cited by examiner

Fig. 26

| Data operation (R) | Execute (A) | Output (P) | Setting (S) | Window (W) |

Register reference distribution map (R) ▶

RBC
PLT
DIFF
PLT−O

US 9,322,834 B2

SAMPLE ANALYZER, BLOOD ANALYZER AND DISPLAYING METHOD

This application claims priority under 35 U.S.C. §119 to Japanese Patent Application No. JP2007-143435 filed May 30, 2007 and Japanese Patent Application No. JP2007-170008 filed Jun. 28, 2007, the entire content of which is hereby incorporated by reference.

FIELD OF THE INVENTION

The present invention relates to a sample analyzer for analyzing a sample containing particles such as blood cells and urine cells, a blood analyzer for analyzing blood, and a method of displaying a particle distribution map representing a distribution state of the particles contained in the sample.

BACKGROUND

An analyzer for analyzing a sample containing particles is conventionally known. For example, U.S. Patent Application Publication No. 2006-004530 discloses a specimen analyzer for electrically or optically detecting each particle such as red blood cell and white blood cell in a blood sample, and creating a one-dimensional frequency distribution map (histogram) or a two-dimensional scattergram using characteristic parameter information representing characteristics of each particle.

The specimen analyzer disclosed in U.S. Patent Application Publication No. 2006-004530 includes a display, where an analysis result display screen for displaying the analysis result of the blood sample is displayed on the display, as shown in FIG. 9 of the document. The number of particles, such as red blood cells contained in the measured blood sample, and the particle distribution map (histogram or scattergram) created in the above manner are shown on the analysis result display screen. When such analysis result display screen is displayed, the user can know about the number of particles such as the red blood cells contained in the measured blood sample, and can visually recognize the distribution state of the particles in the particle distribution map.

However, it is not easy for the user to look at the distribution state of the particles in the particle distribution map and evaluate whether such distribution state is abnormal or normal. Therefore, a reference particle distribution map which becomes an index for making an evaluation on the distribution state is desired to be displayed on the display.

In order to respond to such demand, a particle distribution map representing the distribution state of particles contained in the blood sample taken from a healthy subject may be displayed as the reference particle distribution map next to the particle distribution map of the measured sample. However, since the display area in the analysis result display screen as shown in FIG. 9 of U.S. Patent Application Publication No. 2006-004530 is limited, the display area for displaying information other than the particle distribution map becomes small if such method is used. If the display of each particle distribution map arranged side by side is reduced to ensure the display area for displaying information other than the particle distribution map, the distribution state of the particles in the particle distribution map becomes difficult to visually recognize.

Furthermore, U.S. Pat. No. 6,246,786 discloses a blood analyzer for storing region patterns in which a region where specific particles such as "lymph cells" and "monocytes" appear is surrounded by a region line for the normal blood sample in advance in a memory in correspondence to the coordinate system of the distribution map, and displaying the same on the display with the distribution map of the measured blood sample in order to facilitate the user evaluating whether the measured blood sample is normal or abnormal. According to such display, the user can visually recognize whether or not the lymph cells or the monocytes in the measured blood sample appear within the region pattern in the normal blood sample.

In recent years, analysis of blood samples of animals other than human being is being carried out in veterinary hospitals, livestock experimental station, and the like. In the case of human being, blood test is widely carried out as one item of health examination and great amount of normal blood cell distribution maps and abnormal blood cell distribution maps are stored as analysis data of the blood sample, whereas in the case of animals, the analysis data of the blood sample may not be stored or analyzed depending on the species. The evaluation of one analysis data may differ depending on the species of animals.

Therefore, when analyzing blood samples of animals other than human being, it is difficult to create in advance the region patterns for the normal blood sample, and displaying the region pattern along with the distribution map of the measured blood sample as in the analyzer disclosed in U.S. Pat. No. 6,246,786.

However, in the case of analyzing the blood sample of animals other than human being, it is desired that the user can easily make an evaluation on whether the blood sample is normal or abnormal by looking at the distribution map of the measured blood sample.

SUMMARY

A first aspect of the present invention is a sample analyzer for analyzing a sample containing particles, comprising: a display; a measurement section for measuring a sample containing particles; and a controller in communication with the display and the measurement section, the controller being configured to 1) generate a particle distribution map representing a distribution of the particles contained in the sample, based on measurement data obtained by the measurement section; and 2) control the display so as to display the particle distribution map of the sample at a predetermined display position and to display a reference particle distribution map at the predetermined display position so as to be visually compared with the particle distribution map of the sample.

A second aspect of the present invention is a sample analyzer for analyzing a sample containing particles, comprising: a display; a measurement section for measuring a sample containing particles; generating means for generating a particle distribution map representing a distribution of the particles contained in the sample, based on measurement data obtained by the measurement section; and display controlling means for controlling the display so as to display the particle distribution map of the sample at a predetermined display position and to display a reference particle distribution map at the predetermined display position so as to be visually compared with the particle distribution map of the sample.

A third aspect of the present invention is a method for displaying a particle distribution map representing a distribution of particles contained in a sample, comprising steps of: (a) generating a particle distribution map representing a distribution of particles contained in a sample by measuring the sample containing the particles and displaying the particle distribution map at a predetermined display position; and (b) displaying a reference particle distribution map at the predetermined display position so as to be visually compared with the particle distribution map of the sample.

A fourth aspect of the present invention is a blood analyzer for analyzing blood samples of a plurality of species of animals, comprising: a display; a measurement section for measuring a blood sample; and a controller in communication with the display and the measurement section, the controller being configured to 1) accept a selection of an animal species to be measured; 2) generate a blood cell distribution map representing a distribution of blood cells contained in the blood sample, based on measurement data obtained by the measurement section; and 3) control the display so as to display the blood cell distribution map of the blood sample and a reference blood cell distribution map corresponding to the selected animal species so as to be visually compared.

A fifth aspect of the present invention is a blood analyzer for analyzing blood samples of a plurality of species of animals, comprising: a display; a measurement section for measuring a blood sample; and accepting means for accepting a selection of an animal species to be measured; generating means for generating a blood cell distribution map representing a distribution of blood cells contained in the blood sample, based on measurement data obtained by the measurement section; and display controlling means for controlling the display so as to display the blood cell distribution map of the blood sample and a reference blood cell distribution map corresponding to the selected animal species so as to be visually compared.

A sixth aspect of the present invention is a method for displaying a blood cell distribution map in a blood analyzer for analyzing blood samples of a plurality of species of animals, comprising steps of: a) selecting an animal species to be measured; b) generating a blood cell distribution map representing a distribution of the blood cells contained in the blood sample by measuring the blood sample; and c) displaying the generated blood cell distribution map and a reference blood cell distribution map corresponding to the animal species selected in step a) so as to be visually compared.

BRIEF DESCRIPTION OF THE DRAWINGS

FIG. 26 is a view showing a hierarchical menu for making registration instruction of the reference particle distribution map;

DETAILED DESCRIPTION OF THE EMBODIMENT

The embodiment of the present invention will now be described with reference to the drawings.

[Overall Configuration]

Figure 1:
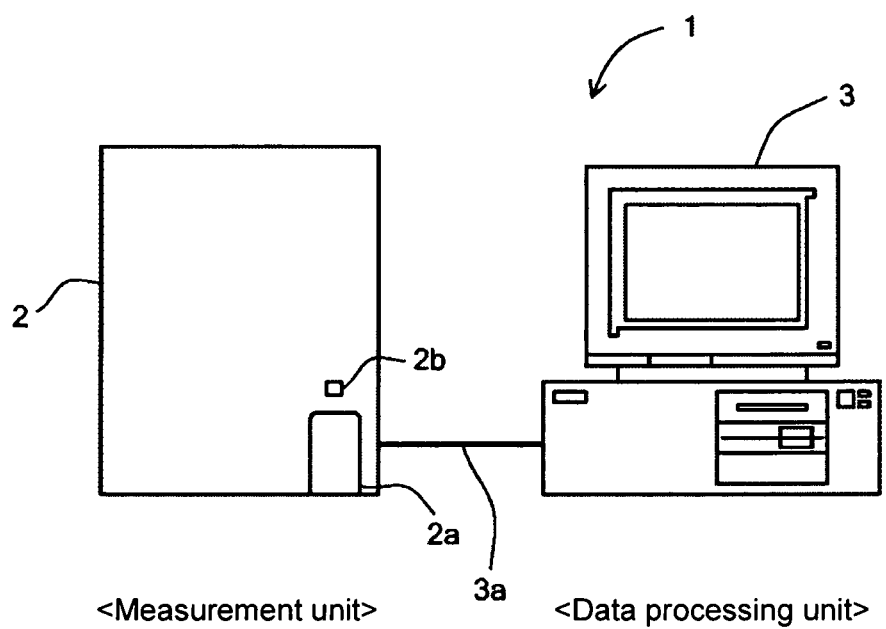
FIG. 1 is a front view showing a schematic configuration of a blood analyzer according to an embodiment of the present invention.

A blood analyzer 1 according to the present embodiment is an analyzer for analyzing the blood of an animal other than a human such as dogs, cats, cows, and horses. As shown in FIG. 1, the blood analyzer 1 is mainly configured by a measurement unit 2 and a data processing unit 3, where a predetermined measurement on the components contained in the blood is performed by the measurement unit 2, and the measurement data is received by the data processing unit 3 to perform data processing. The measurement unit 2 and the data processing unit 3 are connected by a data transmission cable 3a so as to be data communicable with each other.

[Measurement Unit]

Figure 2:
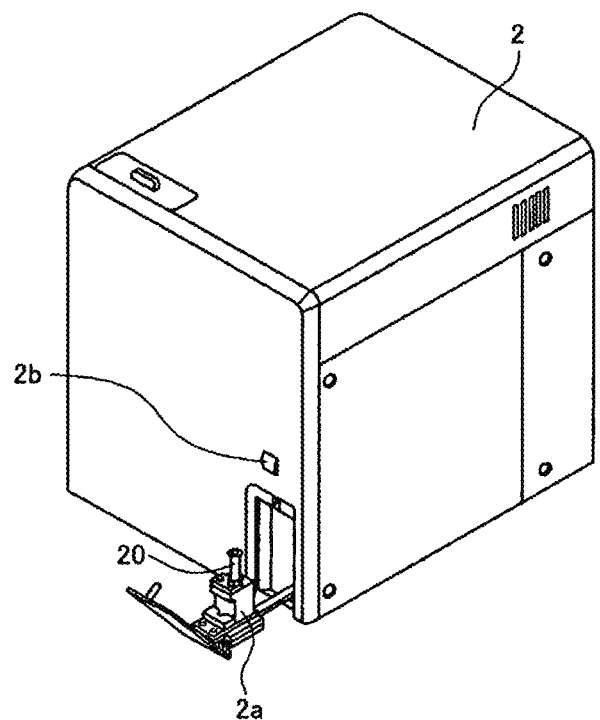
FIG. 2 is a perspective view showing an outer appearance of a measurement unit.

As shown in FIG. 2, a blood collecting tube set part 2a capable of setting a blood collecting tube 20 containing blood is arranged at the lower right portion on the front face of the measurement unit 2. The blood collecting tube set part 2a opens forward and projects out when the user pushes a button switch 2b arranged in the vicinity thereof, in which state the user is able to set the blood collecting tube 20. After the blood collecting tube 20 is set, the user again pushes the button switch 2b so that the blood collecting tube set part 2a moves backward and closes.

Figure 3:
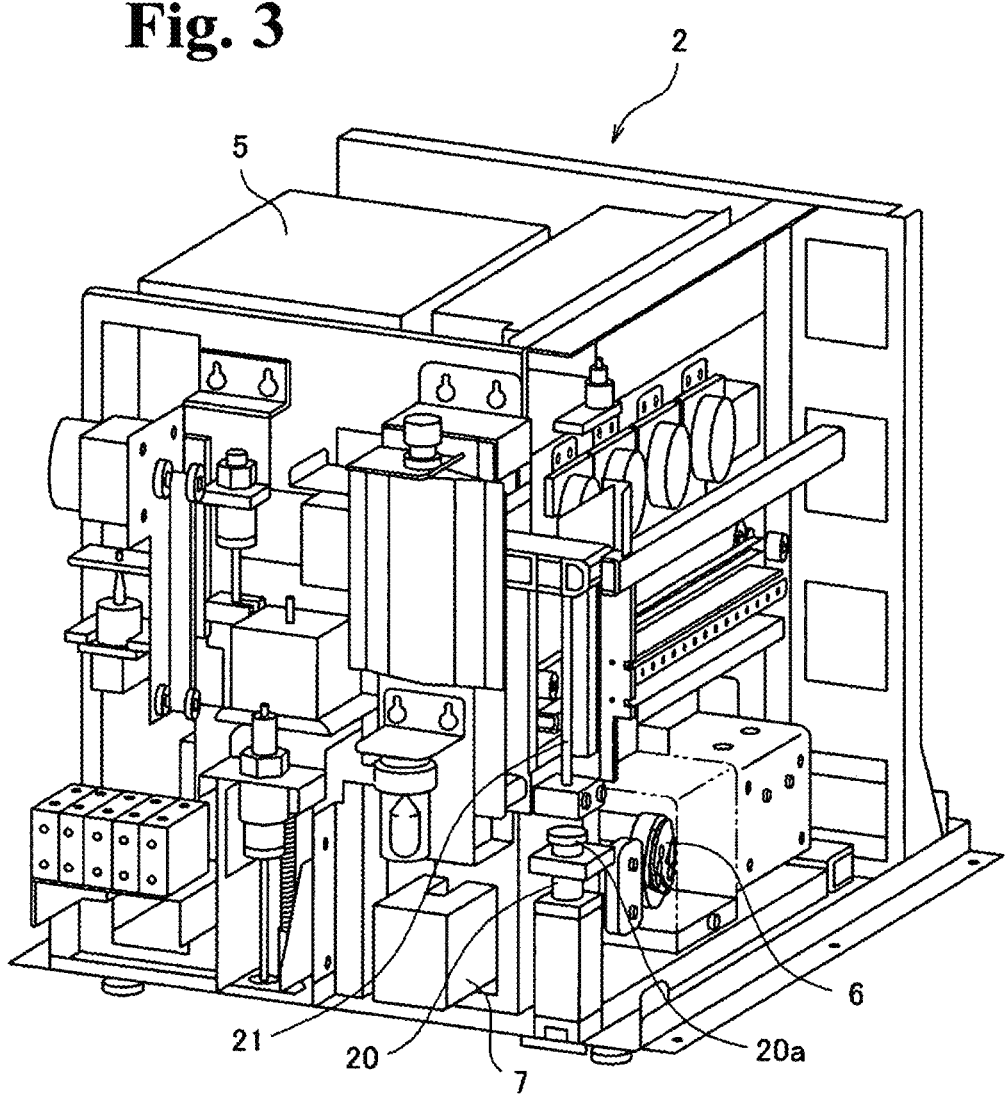
FIG. 3 is a perspective view showing an inner structure of the measurement unit.
Figure 4:
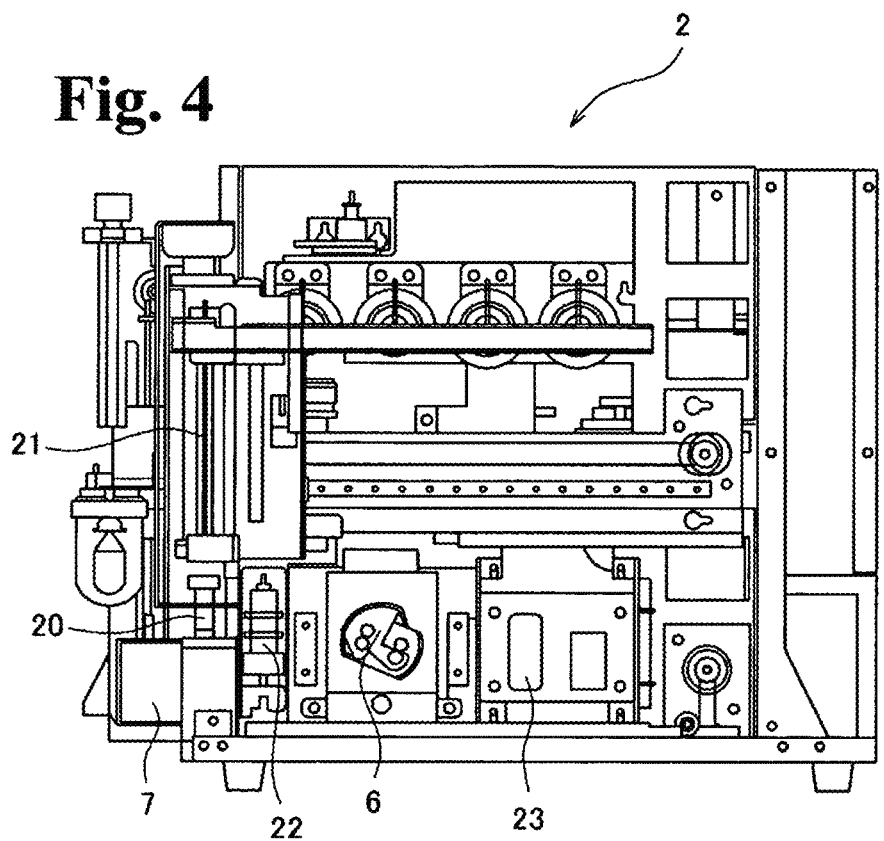
FIG. 4 is a side view of the measurement unit shown in FIG. 3.

As shown in FIGS. 3 and 4, the blood collecting set part 2a set with the blood collecting tube 20 is accommodated inside the measurement unit 2 as described above, and the blood collecting tube 20 is positioned at a predetermined aspirating position. A sample preparing section 4 including a pipette 21 for aspirating the blood, chambers 22, 23 for mixing and preparing the blood and the sample is arranged inside the measurement unit 2. The pipette 21 is formed to a tubular shape extending in the up and down direction, and has a sharp pointed tip. The pipette 21 is connected to a syringe pump (not shown) to aspirate and discharge liquid by a predetermined amount by the operation of the syringe pump. The pipette 21 is connected to a movement mechanism to be movable in the up and down direction and in the front and back direction. The blood collecting tube 20 is sealed by a rubber cap 20a, whereby the pointed tip of the pipette 21 perforates through the cap 20a of the blood collecting tube 20 set at the aspirating position and the pipette 21 aspirates the blood contained in the blood collecting tube 20 by a predetermined amount. As shown in FIG. 4, the chambers 22, 23 are arranged on the rear side of the blood collecting tube set part 2a, so that the pipette 21 that has aspirated the blood is moved to above the chambers 22, 23 by the movement mechanism, and is caused to discharge the blood into the chambers 22, 23 to supply blood into the chambers 22, 23.

Figure 5:
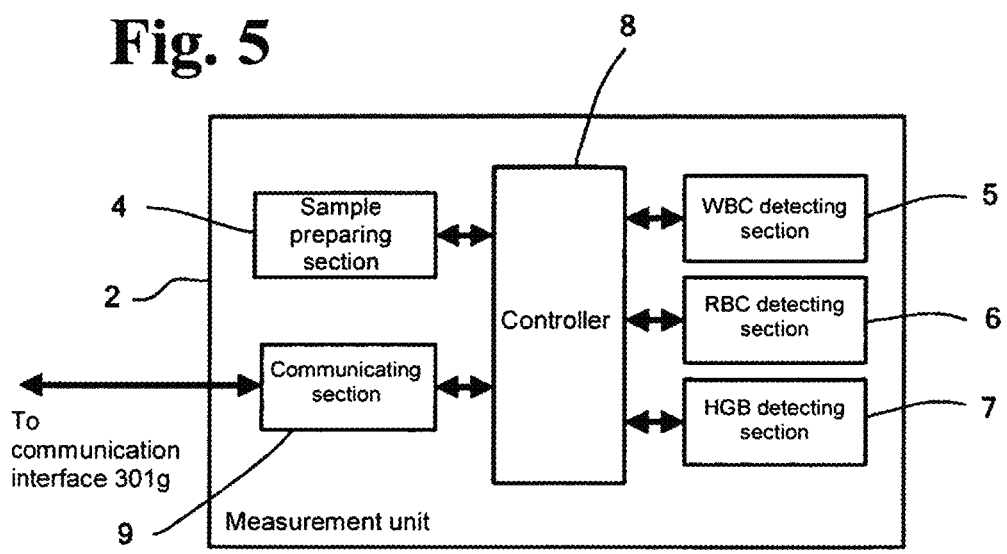
FIG. 5 is a block diagram showing a configuration of the measurement unit.

As shown in FIG. 5, the measurement unit 2 includes a sample preparing section 4, a WBC detecting section 5, a RBC/PLT detecting section 6, an HGB detecting section 7, a controller 8, and a communicating section 9. The controller 8 is configured by a CPU, a ROM, a RAM, and the like, and performs operation control of each component of the measurement unit 2. The communicating section 9 is an RS-232C interface that transmits and receives data with the data processing unit 3.

[Sample Preparing Section]

Figure 6:
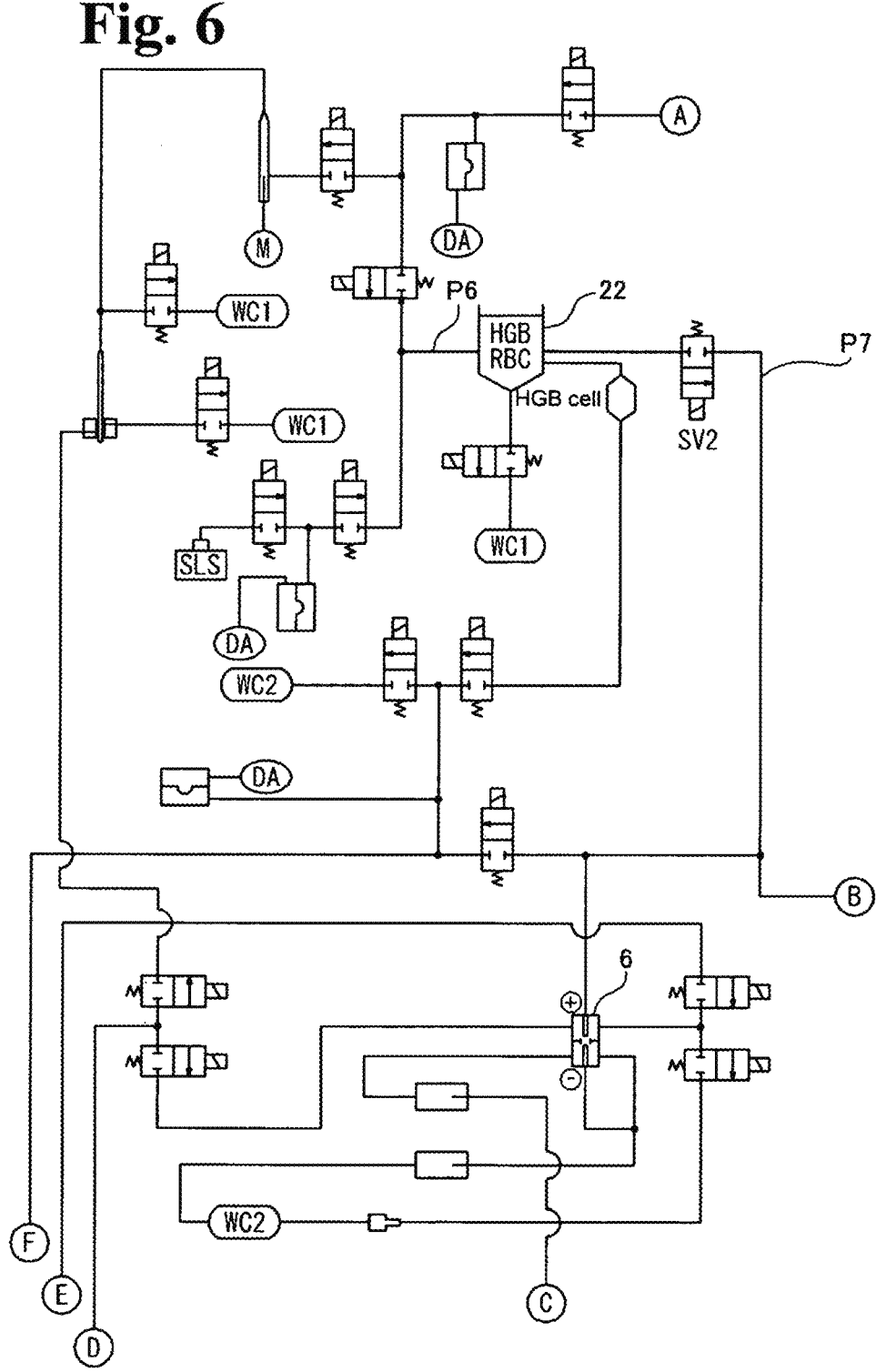
FIGS. 6 and 7 are fluid circuit diagrams showing a configuration of a sample preparing section.
Figure 7:
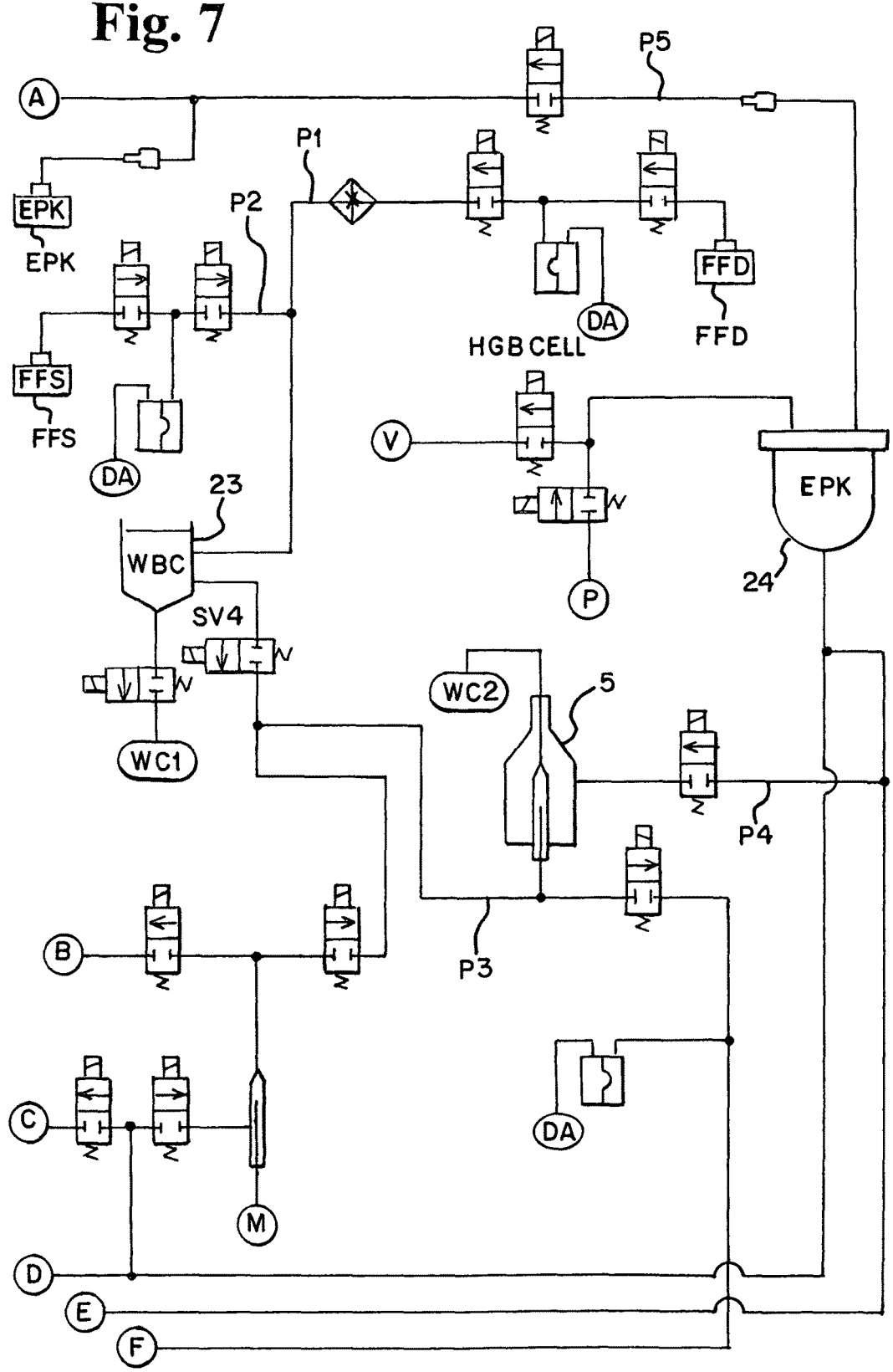

As shown in FIGS. 6 and 7, the sample preparing section 4 is a fluid unit including a chamber, a plurality of electromagnetic valves, a diaphragm pump, and the like. The chamber 22 shown in FIG. 6 is used to prepare a measurement sample to be supplied for measurement of red blood cells and blood platelets, and for measurement of hemoglobin. The chamber 22 is connected to a reagent container EPK containing diluting solution shown in FIG. 7 by way of a fluid communication path P6 such as a tube. The chamber 23 is used to prepare a measurement sample to be supplied for measurement of white blood cells. The chamber 23 is connected to a reagent container FFD containing hemolytic agent and a reagent container FFS containing staining fluid by way of fluid communication paths P1, P2 such as a tube. The chamber 22 is connected to the RBC/PLT detecting section 6 by way of a fluid communication path P7 including a tube and an electromagnetic valve SV2. The chamber 23 is connected to the WBC detecting section 5 by way of a fluid communication path P3 including a tube and an electromagnetic valve SV4. A sheath liquid chamber 24 is further arranged in the sample preparing section 4, which sheath liquid chamber 24 is connected to the WBC detecting section 5 by way of a fluid communication path P4.

[WBC Detecting Section]

Figure 8:
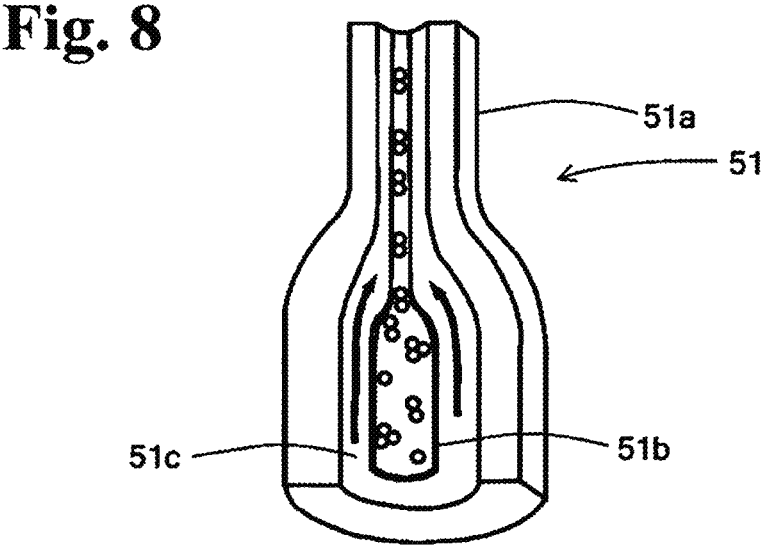
FIG. 8 is a perspective view showing in frame format a configuration of a flow cell.

The WBC detecting section 5 is an optical flow cytometer capable of measuring the white blood cells through a flow cytometry method by a semiconductor laser. The WBC detecting section 5 includes a flow cell 51 forming a liquid current of the measurement sample. As shown in FIG. 8, the flow cell 51 is configured to a tubular shape by materials such as quartz, glass, synthetic resin, and the like having translucency, the inside of which is a flow channel for the measurement sample and the sheath liquid to flow through. An orifice 51a having the internal space squeezed narrower than other portions is arranged on the flow cell 51. The vicinity of the inlet of the orifice 51a of the flow cell 51 has a double tubular structure, and the inner tube portion thereof acts as a sample nozzle 51b. The sample nozzle 51b is connected to the fluid communication path P3 of the sample preparing section 4, and the measurement sample is discharged from the sample nozzle 51b. The space on the outer side of the sample nozzle 51b is a flow channel 51c through which the sheath liquid flows, which flow channel 51a is connected to the fluid communication path P4 described above. The sheath liquid supplied from the sheath liquid chamber 24 flows through the flow channel 51c through the fluid communication path P4, and introduced into the orifice 51a. The sheath liquid supplied to the flow cell 51 thus flows so as to surround the measurement sample discharged from the sample nozzle 51b. The flow of the measurement sample is narrowed by the orifice 51a, and the particles such as white blood cells and red blood cells contained in the measurement sample pass through the orifice 51a one at a time while being surrounded by the sheath liquid.

Figure 9:
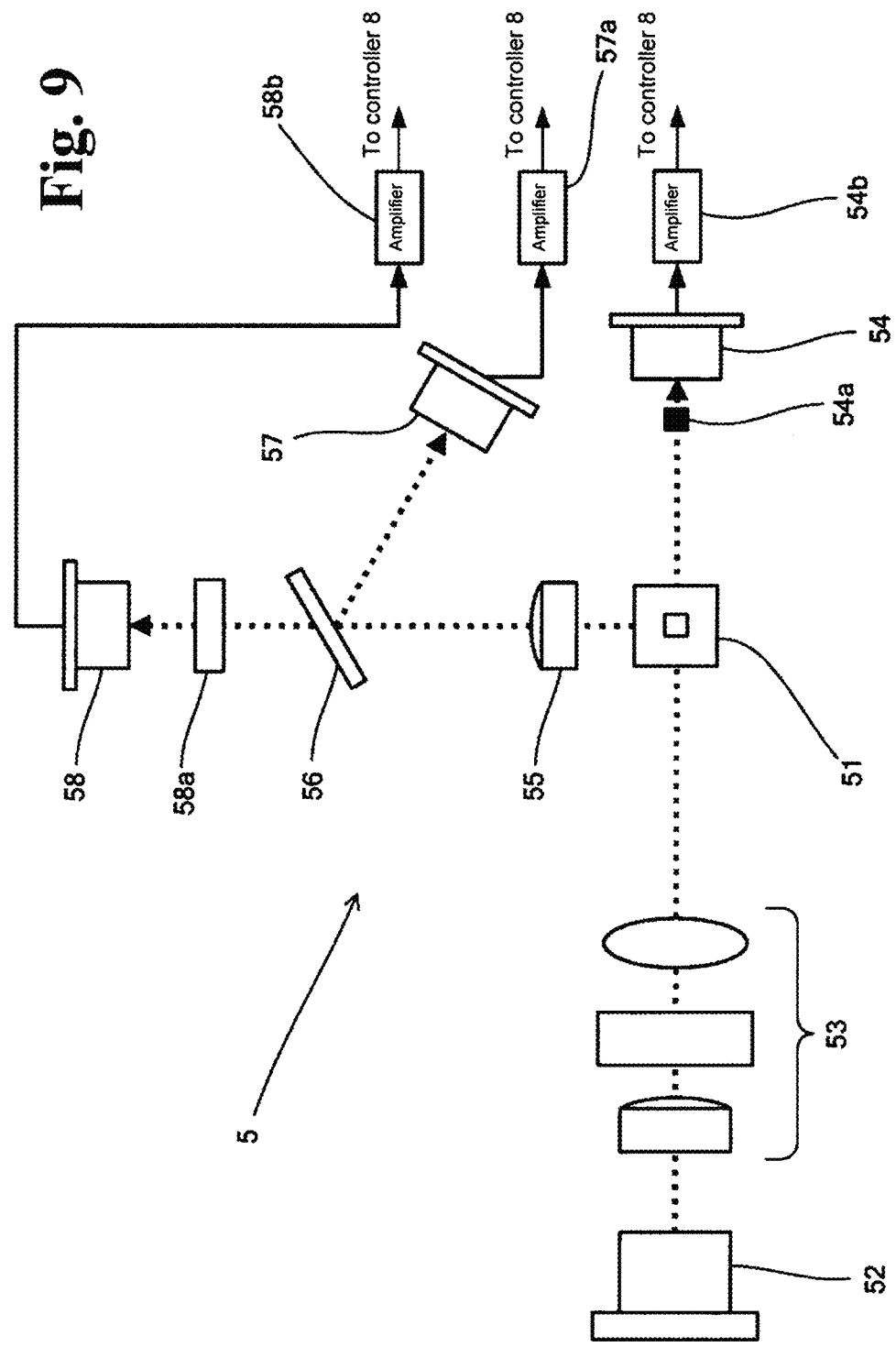
FIG. 9 is a schematic plan view showing in frame format the configuration of the WBC detecting section.

As shown in FIG. 9, a semiconductor laser light source 52 is arranged in the WBC detecting section 5 so as to emit the laser light towards the orifice 51a of the flow cell 51. An irradiation lens system 53 including a plurality of lenses is arranged in the semiconductor laser light source 52 and the flow cell 51. The parallel beam emitted from the semiconductor laser light source is converged to a beam spot by the irradiation lens system 53. A beam stopper 54a is arranged on the optical axis linearly extending from the semiconductor laser light source 52 so as to face the irradiation lens system 53 with the flow cell 51 sandwiched in between, and the direct light from the semiconductor laser light source 52 is shielded by the beam stopper 54a. A photodiode 54 is arranged further on the downstream side of the beam stopper 54a.

When the measurement reagent flows to the flow cell 51, optical signals of scattered light and fluorescent light generate by the laser light. The forward signal lights are irradiated towards the photodiode 54. Among the lights advancing along the optical axis linearly extending from the semiconductor laser light source 52, the direct light of the semiconductor laser light source 52 is shielded by the beam stopper 54a, and substantially only the scattered light (hereinafter referred to as forward scattered light) advancing along the optical axis direction enter the photodiode 54. The forward scattered light emitted from the flow cell 51 is photoelectric converted by the photodiode 54, and the electric signal generated therefrom (hereinafter referred to as forward scattered optical signal) is amplified by an amplifier 54b and output to the controller 8. Such forward scattered optical signal reflects the size the blood cells, and the size etc. of the blood cell can be obtained when the forward scattered optical signal is signal processed by the controller 8.

A side light collecting lens 55 is arranged on the side of the flow cell 51 in a direction orthogonal to the optical axis linearly extending from the semiconductor laser light source 52 to the photodiode 54, so that the side light (light emitted in a direction intersecting the optical axis) generated when the semiconductor laser is irradiated on the blood cell passing through the flow cell 51 is collected by the side light collecting lens 55. A dichroic mirror 56 is arranged on the downstream side of the side light collecting lens 55, where the signal light sent from the side light collecting lens 55 is divided into the scattered light component and the fluorescent light component by the dichroic mirror 56. A photodiode 57 for side scattered light reception is arranged on the side of the dichroic mirror 56 (direction intersecting the optical axis direction connecting the side light collecting lens 55 and the dichroic mirror 56), and an optical filter 58a and an avalanche photodiode 58 are arranged on the downstream side of the optical axis of the dichroic mirror 56. The side scattered light component divided by the dichroic mirror 56 is photoelectric converted by the photodiode 57, and the electric signal generated therefrom (hereinafter referred to as side scattered optical signal) is amplified by an amplifier 57a, and output to the controller 8. The side scattered optical signal reflects internal information of the blood cell (size of core, and the like), and the size of the core etc. of the blood cell can be obtained when the side scattered optical signal is signal processed by the controller 8. Furthermore, the side fluorescent light component generated from the dichroic mirror 56 is wavelength selected by the optical filter 58*a*, and thereafter, photoelectric converted by the avalanche photodiode 58, and the electric signal generated therefrom (hereinafter referred to as side fluorescent optical signal) is amplified by an amplifier 58*b*, and output to the controller 8. The side fluorescent optical signal reflects information related to the stain degree of the blood cell, and the stainability etc. of the blood cell can be obtained when the side fluorescent optical signal is signal processed by the controller 8.

[RBC/PLT Detecting Section]

The RBC/PLT detecting section 6 can measure the number of red blood cells and the number of blood platelets through sheath flow DC detection method. The RBC detecting section 6 includes a flow cell (not shown), where the measurement sample is supplied from the chamber 22 to such flow cell. When measuring the red blood cells and the blood platelets, the diluting solution is mixed with blood in the chamber 22 to prepare the measurement sample. Such measurement sample is supplied to the flow cell from the sample preparing section 4 along with sheath liquid, so that liquid current in which the measurement sample is surrounded by sheath liquid forms in the flow cell. An aperture having an electrode is arranged in the middle of the flow channel in the flow cell, which aperture detects the DC resistance in the aperture when the blood cell in the measurement sample passes through the relevant aperture one at a time, and outputs the electric signal to the controller 8. The DC resistance increases when the blood cell passes through the aperture, and thus the electric signal reflects the pass-through information of the blood cell in the aperture, and the red blood cells and the blood platelets can be counted by signal processing the electric signal.

Discrimination of the red blood cells and the blood platelets can be satisfactorily performed using the RBC/PLT detecting section 6 or an electrical detecting section when measuring the blood of a human, but discrimination of the red blood cells and the blood platelets may not be satisfactorily performed with only the RBC/PLT detecting section 6 in the case of measuring the blood of an animal. Thus, the blood analyzer 1 of the present embodiment is configured to measure the measurement sample for the red blood cell and the blood platelet measurement with both the RBC/PLT detecting section 6 of the electrical detecting section and the WBC detecting section 5 or the optical detecting section.

[HGB Detecting Section]

The HGB detecting section 7 can measure the hemoglobin content through the SLS hemoglobin method. A cell for containing the diluted sample is arranged in the HGB detecting section 7, and the sample from the chamber 22 is supplied to the cell. When measuring hemoglobin, the diluting solution and the hemolytic agent are mixed with blood in the chamber 22 to prepare the measurement sample. The hemolytic agent has a property of transforming hemoglobin in the blood to SLS-hemoglobin. The light emitting diode and the photodiode are arranged facing each other with the cell in between, so that the light from the light emitting diode is received by the photodiode. The light emitting diode emits light of a wavelength having high absorption by the SLS-hemoglobin, and the cell is made of plastic material having high translucency. Thus, the transmitted light in which the emitted light of the light emitting diode is more or less absorbed only by the measurement sample is received by the photodiode. The photodiode outputs an electric signal corresponding to the light received amount (absorption) to the controller 8, and the controller 8 compares such absorption and the absorption of only the diluting solution measured in advance and calculates a hemoglobin value.

The controller 8 thus receives the electric signals from the WBC detecting section 5, the RBC/PLT detecting section 6, and the HGB detecting section 7, and transmits measurement data representing the size of the blood cell, the size of the core of the blood cell, the stainability of the blood cell, the number of red blood cells, the number of blood platelets, the hemoglobin value, and the like to the data processing unit 3 via the communicating section 9.

[Data Processing Unit]

Figure 10:
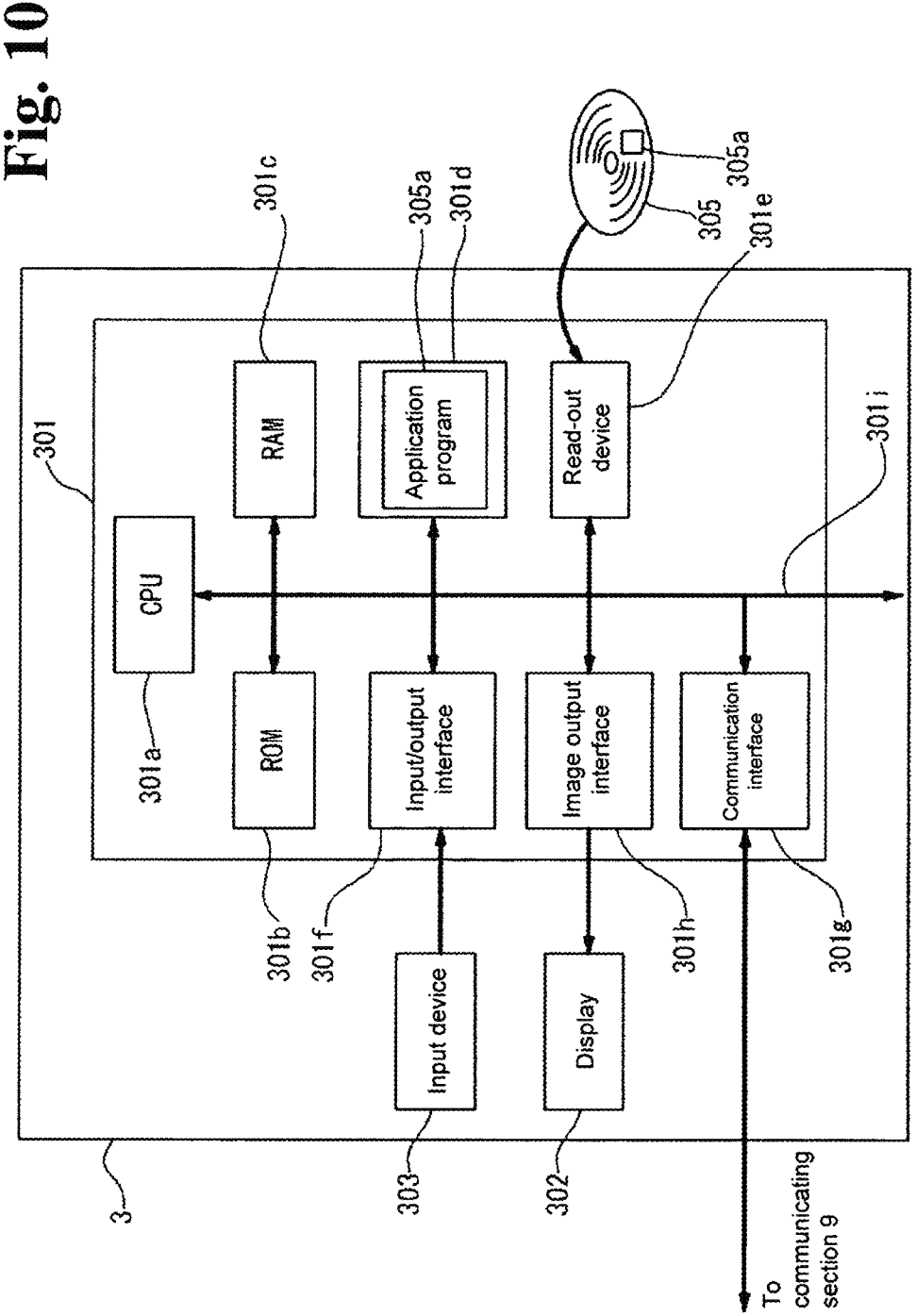
FIG. 10 is a block diagram showing the configuration of the data processing unit.

As shown in FIG. 10, the data processing unit 3 is configured by a computer mainly consisting of a main body 301, a display 302, and an input device 303. The main body 301 is mainly configured by a CPU 301*a*, a ROM 301*b*, a RAM 301*c*, a hard disc 301*d*, a read-out device 301*e*, an input/output interface 301*f*, an image output interface 301*h*, and a communication interface 301*g*, where the CPU 301*a*, the ROM 301*b*, the RAM 301*c*, the hard disc 301*d*, the read-out device 301*e*, the input/output interface 301*f*, the image output interface 301*h*, and the communication interface 301*g* are data communicably connected by a bus 301*i*.

The CPU 301*a* executes computer programs stored in the ROM 301*b* and the computer programs loaded in the RAM 301*c*. The computer serves as the data processing unit 3 when the CPU 301*a* executes the application program 305*a*, as hereinafter described.

The ROM 301*b* is configured by mask ROM, PROM, EPROM, EEPROM, and the like, and is recorded with computer programs to be executed by the CPU 301*a*, data used for the same, and the like.

The RAM 301*c* is configured by SRAM, DRAM, and the like. The RAM 301*c* is used to read out the computer programs recorded on the ROM 301*b* and the hard disc 301*d*. The RAM 301*c* is used as a work region of the CPU 301*a* when executing the computer programs.

The hard disc 301*d* is installed with various computer programs to be executed by the CPU 301*a* such as operating system and application program, as well as data used in executing the computer program. The application program 305*a* to be hereinafter described is also installed in the hard disc 301*d*.

The read-out device 301*e* is configured by flexible disc drive, CD-ROM drive, DVD-ROM drive, and the like, and is able to read out computer programs and data recorded on a portable recording medium 305. The application program 305*a* for causing the computer to realize a predetermined function is stored in the portable recording medium 305, where the computer serving as the data processing unit 3 reads out the application program 305*a* from the portable recording medium 305, and installs the application program 305*a* to the hard disc 301*d*.

The application program 305*a* is not only provided by the portable recording medium 305, but also provided through communication line (wired or wireless) from external devices communicatably connected with the data processing unit 3 through the communication line. For instance, the application program 305*a* may be stored in the hard disc of the server computer on the Internet, so that the data processing unit 3 can access the server computer to download the computer program and install the computer program to the hard disc 301*d*.

Operating system providing graphical user interface environment such as Windows (registered trademark) manufactured and sold by US Microsoft Co. is installed in the hard disc 301*d*. The application program 305*a* according to the present embodiment is assumed to operate on the operating system.

The input/output interface 301*f* is configured by serial interface such as USB, IEEE1394, RS-232C; parallel interface such as SCSI, IDE, IEEE1284; analog interface such as D/A converter, A/D converter, and the like. The input device 303 including a keyboard and a mouse is connected to the input/output interface 301*f*, so that the user can input data to the data processing unit 3 using the input device 303.

The image output interface 301*h* is connected to the display 302 configured by LCD, CRT, or the like, and is configured to output an image signal corresponding to the image data provided from the CPU 301*a* to the display 302. The display 302 displays the image (screen) according to the input image signal.

The communication interface 301*g* is, for example, Ethernet (registered trademark) interface. The data processing unit 3 transmits and receives data with the measurement unit 2 using a predetermined communication protocol by means of the communication interface 301*g*.

The data processing unit 3 executes the application program 305*a* on the CPU 301*a* to process the measurement data received from the measurement unit 2, and calculate the number if white blood cells (WBC), the number of red blood cells (RBC), the hemoglobin content (HGB), the hematocrit value (HCT), the average red blood cell volume (MCV), the average red blood cell hemoglobin content (MCH), the average red blood cell hemoglobin concentration (MCHC), the number of blood platelets (PLT), and the like. The data processing unit 3 can create various two-dimensional scattergrams a histograms (one-dimensional frequency distribution map) using the measurement data received from the measurement unit 2.

The data processing unit 3 can stored in advance in the hard disc 301*d* a plurality of reference particle distribution maps (reference scattergrams and histograms) corresponding to the animal species to be analyzed by the blood analyzer 1. The reference particle distribution map is a particle distribution map displayed on the display 302 to be compared with the particle distribution map of the measured specimen, and serves as an index for determining whether the measured specimen is normal or abnormal.

The user of the blood analyzer 1 inputs the animal species of the specimen measured by the measurement unit 2 using the input device 303 of the data processing unit 3. The data processing unit 3 has a function of displaying a screen for the user to select the animal species (e.g., dog, cat, horse, and the like) on the display 302, and a function of accepting the input signal for selecting the animal species from the input device 303 such as keyboard and mouse.

[Processes by Measurement Unit and Data Processing Unit]

Figure 11:
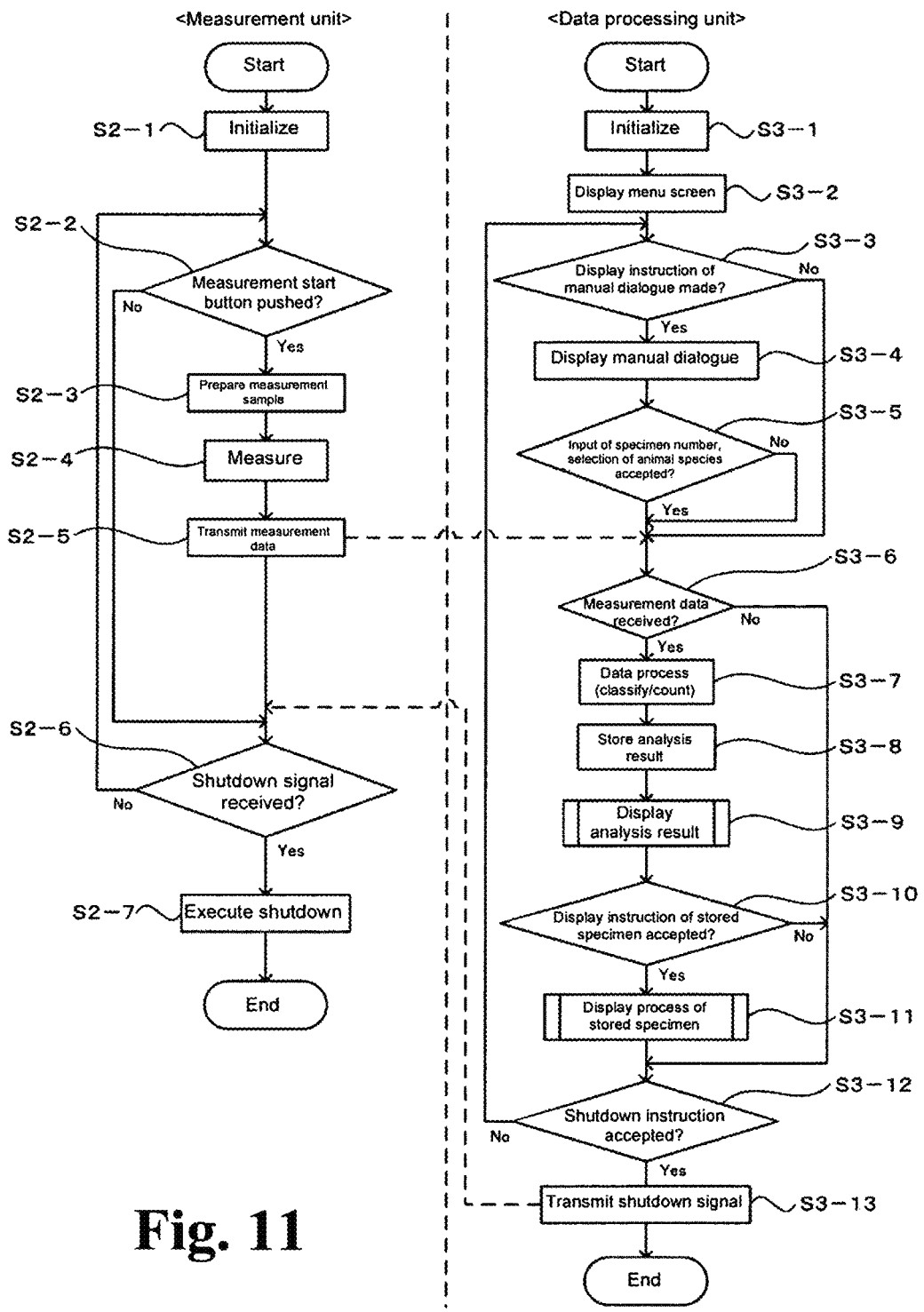
FIG. 11 is a flowchart showing a flow of process of the measurement unit and the data processing unit.
Figure 12:
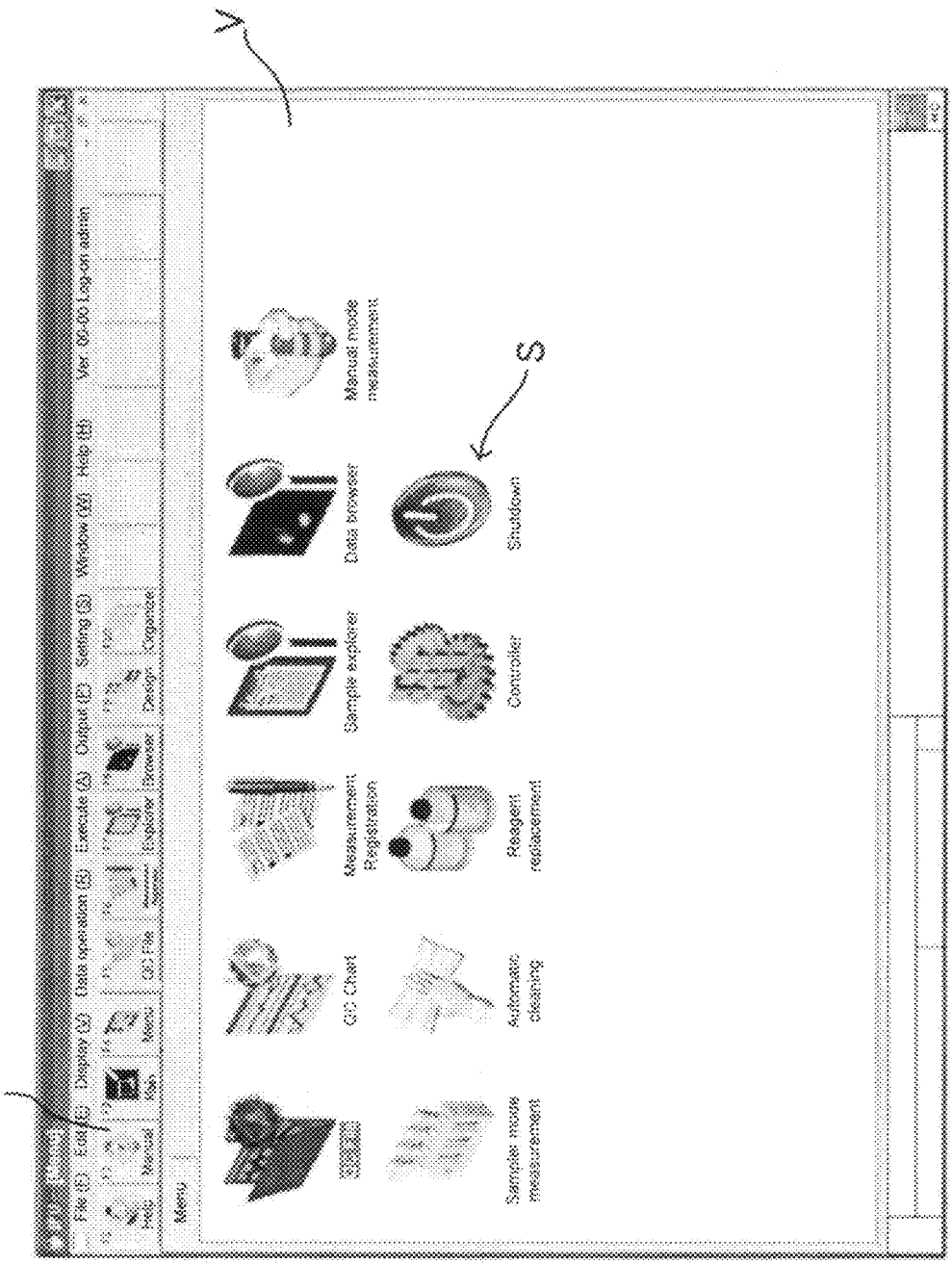
FIG. 12 is a view showing a menu screen.

The flow of process in the measurement unit 2 and the data processing unit 3 will now be described using FIG. 11. First, when the powers of the measurement unit 2 and the data processing unit 3 are turned ON by the operation of the user, initialization of each mechanism of the measurement unit 2 and initialization of the computer programs and the like stored in the data processing unit 3 are performed (steps S2-1, S3-1). Subsequently, the CPU 301*a* of the data processing unit 3 displays a menu screen shown in FIG. 12 on the display 302 through the image output interface 301*h* (step S3-2). As shown in FIG. 12, a tool bar (icon display region) T, a view (function screen region) V, and the like are arranged in the menu screen.

The CPU 301*a* of the data processing unit 3 then determines whether or not a display instruction of a manual dialogue is made (step S3-3). Specifically, the CPU 301*a* determines whether or not "manual" button T1 arranged in the tool bar T of the menu screen shown in FIG. 12 or an analysis result screen shown in FIG. 19, 28, or 29 to be hereinafter described is clicked by the user. If the display instruction of the manual dialogue is made, the CPU 301*a* displays a manual dialogue shown in FIG. 13 on the display 302 through the image output interface 301*h* (step S3-4).

Figure 13:
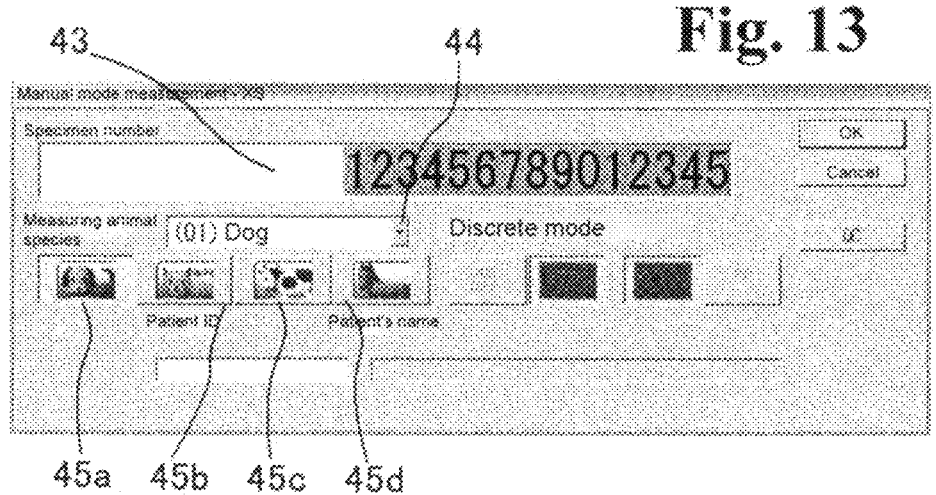
FIG. 13 is a view showing a manual dialogue.

After displaying the manual dialogue shown in FIG. 13, the CPU 301*a* determines whether or not input of a specimen number or selection of the animal species of the specimen to be measured from the user is accepted (step S3-5). The CPU 301*a* can accept the input of the specimen number and the selection of the animal species of the specimen to be measured from the user in the manual dialogue. A specimen number input region 43, an animal species switching button 44, and animal species selection icons 45*a* to 45*d* are arranged in the manual dialogue. The user can input the specimen number of the specimen to be measured to the specimen number input region 43 using the keyboard. Dog is assigned to the animal species selection icon 45*a* of the manual dialogue, cat to 45*b*, cow to 45*c*, and horse to 45*d*, and an assigned animal species is illustrated for the respective icons. If the animal species to be measured is found in the four icons, the user clicks the icon of the relevant animal species using the mouse to select such animal species as the measuring target (measuring animal species). Here, only the icon selected for the measuring animal species is displayed in color and the other icons are displayed in black and white, and thus the user can easily recognize which measuring animal species is being selected. When setting the animal species other than the four animal species as the measuring animal species, the user clicks the animal species switching button 44 using the mouse. When the animal species switching button 44 is clicked, a pull-down menu (not shown) for selecting the measuring animal species is displayed. When one of the buttons of the animal species displayed on the pull-down menu is clicked, the CPU 301*a* of the data processing unit 3 accepts the animal species assigned to the clicked button as the measuring animal species. The information on the input specimen number and the selected animal species can be stored in the RAM 301*c*. After accepting the input of the specimen number and the selection of the animal species of the specimen to be measured, the CPU 301*a* proceeds to the process of step S3-6. If the input of the specimen number and the selection of the animal species from the user are not accepted (i.e., if display instruction of the manual dialogue is not made in step S3-3, or if input of specimen number and selection of animal species are not accepted in step S3-5), the CPU 301*a* proceeds to the process of step S3-6, and thereafter executes the data process under the analysis conditions corresponding to the animal species (dog in the present embodiment) set in advance as a default in step S3-7. In this case, the specimen number is provided to the specimen to be measured by the CPU 301*a* based on a rule set as a default. A case where cat is selected by the user as the animal species of the specimen to be measured will be described below.

The controller 8 of the measurement unit 2 determines whether or not a measurement start button (not shown) arranged in the measurement unit 2 is pushed (step S2-2).

If the measurement start button is pushed, the controller 8 causes the sample preparing section 4 to prepare the measurement sample for red blood cell and blood platelet measurement (hereinafter referred to as "RBC/PLT measurement sample"), the measurement sample for white blood cell measurement (hereinafter referred to as "WBC measurement sample"), and the measurement sample for hemoglobin measurement (hereinafter referred to as "HGB measurement sample") (step S203). If the measurement start button is not pushed, the controller 8 proceeds to the process of step S206.

The measurement unit 2 then performs the measurement of the RBC/PLT measurement sample, the measurement of the WBC measurement sample, and the measurement of the HGB measurement sample (step S2-4). In the present embodiment, one part of the RBC/PLT measurement sample is measured in the RBC/PLT detecting section 6, and other parts of the RBC/PLT measurement sample are measured in the WBC detecting section 5. The WBC measurement sample is measured in the WBC detecting section 5, and the HGB measurement sample is measured in the HGB detecting section 7.

The controller 8 of the measurement unit 2 transmits the measurement data to the CPU 301a through the communicating section 9 and the communication interface 301g of the data processing unit 3 (step S2-5).

The CPU 301a of the data processing unit 3 determines whether or not the measurement data is received from the controller 8 of the measurement unit 2 (step S3-6), and executes a classifying/counting process of the particles contained in the measurement sample based on the measurement data if the measurement data is received (step S3-7). If the measurement data is not received, the CPU 301a proceeds to the process of step S3-12.

Figure 14:
FIG. 14 is a RBC histogram.
Figure 15:
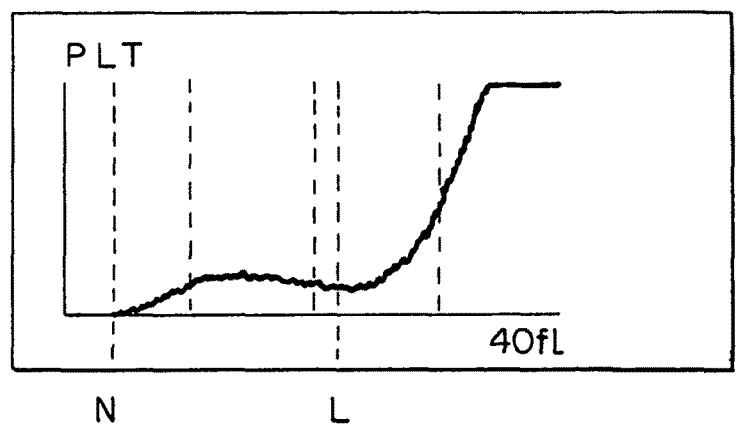
FIG. 15 is a PLT histogram.

In the classifying/counting process of the particles, the CPU 301a of the data processing unit 3 creates a histogram shown in FIGS. 14 and 15 based on the measurement data of the RBC/PLT measurement sample measured in the RBC/PLT detecting section 6. The histogram shown in FIG. 14 is an RBC histogram drawn using the forward scattered light intensity in the X-axis direction and the number of particles in the Y-axis direction. The line L shown in the histogram is a line for discriminating the red blood cells and the blood platelets, where the particles distributed in the region between the line L and a line M are discriminated as red blood cells. FIG. 15 is a PLT histogram showing a region near the line L of the histogram of FIG. 14, where the particles distributed in the region between a line N and the line L are discriminated as blood platelets. The positions of the lines L, M, and N differ according to each animal species, and thus the CPU 301a changes the positions of the lines L, M, N according to the animal species accepted in step S3-5. The RBC histogram of FIG. 14 and the PLT histogram of FIG. 15 are examples of the analysis result displayed on the display 302 in step S901 of FIG. 18 to be hereinafter described.

Figure 16:
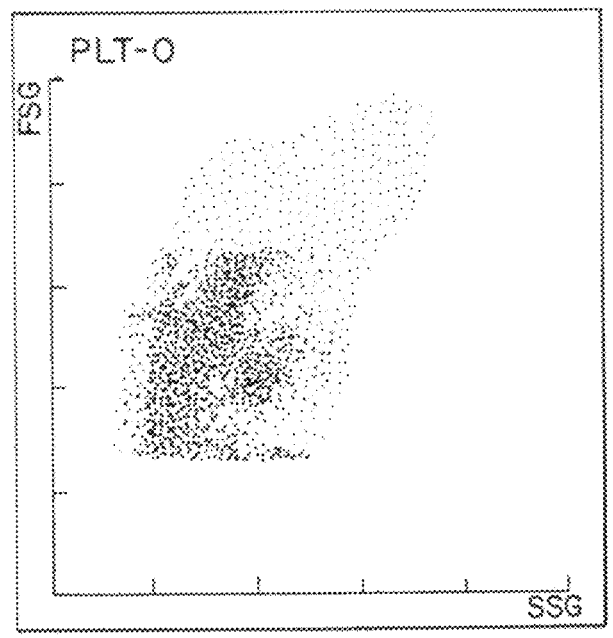
FIG. 16 is a PLT-O scattergram.

In the blood analyzer 1 according to the present embodiment, the RBC/PLT measurement sample is not only measured in the RBC/PLT detecting section 6 or the electrical detecting section but is also measured in the WBC detecting section 5 or the optical detecting section. The CPU 301a of the data processing unit 3 creates a scattergram shown in FIG. 16 based on the measurement data of the RBC/PLT measurement sample measured in the WBC detecting section 5. The scattergram shown in FIG. 16 is a PLT-O scattergram drawn using the side scattered light intensity in the X-axis direction and the forward scattered light intensity in the Y-axis direction, and classifies the red blood cells and the blood platelets (distinction can be made even if the sizes of the blood cells are the same as internal information of the blood cells differ between the red blood cells and the blood platelets). The CPU 301a calculates the ratio between the number of red blood cells and the number of blood platelets based on the scattergram, distributes the total number of particles of the red blood cells and the blood platelets acquired based on the measurement data obtained in the RBC/PLT detecting section 6 to each blood cell using the calculated ratio, and calculates the number of red blood cells and the number of blood platelets. Since the condition for classifying the red blood cells and the blood platelets in the PLT-O scattergram differ according to each animal species, the CPU 301a changes the condition in the PLT-O scattergram according to the animal species accepted in step S3-5. The calculated number of red blood cells and the number of blood platelets, as well as the PLT-O scattergram of FIG. 16 are examples of the analysis result displayed on the display 302 in step S901 of FIG. 18.

Figure 17:
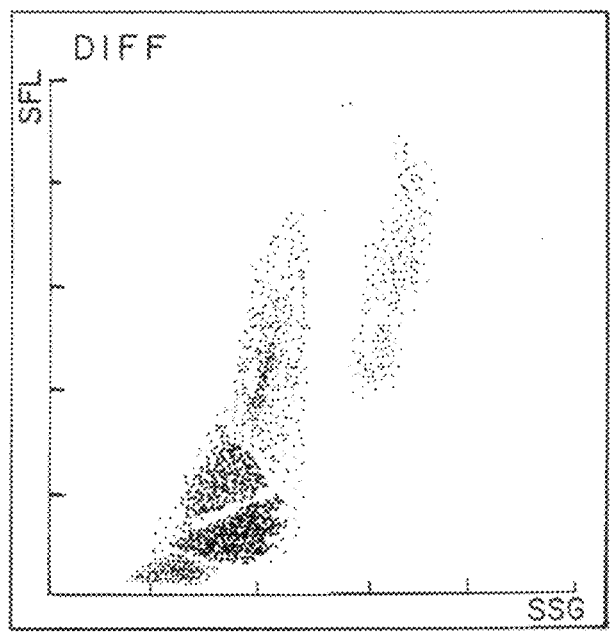
FIG. 17 is a DIFF scattergram.

The CPU 301a of the data processing unit 3 creates a two-dimensional scattergram shown in FIG. 17 based on the measurement data of the WBC measurement sample measured in the WBC detecting section 5. The scattergram shown in FIG. 17 is a DIFF scattergram drawn using the side scattered light intensity in the X-axis direction and the side fluorescent light intensity in the Y-axis direction. The CPU 301a classifies the particles contained in the measurement sample into a cluster of red blood cell ghosts, a cluster of lymph cells, a cluster of monocytes, a cluster of acidophilic leucocytes, and a cluster of neutrophilic leucocytes on the scattergram. The number of particles of each measurement item (lymph cell, monocyte, acidophilic leucocytes, and neutrophilic leucocytes) of the white blood cells is acquired by counting the particles of each cluster. The total number of white blood cells is acquired by adding up the number of particles of each cluster other than the cluster of the red blood cell ghosts. Since the condition for classifying the white blood cells in the DIFF scattergram differ according to each animal species, and the CPU 301a changes the condition in the DIFF scattergram according to the animal species accepted in step S3-5. The acquired number of particles and the DIFF scattergram shown in FIG. 17 are examples of the analysis result displayed on the display 302 in step S901 of FIG. 18 to be hereinafter described.

The CPU 301a stores the analysis result acquired in the above manner in the hard disc 301d (step S308).

The CPU 301a then displays the analysis result stored in the hard disc 301d through the image output interface 301h (step S309). The display process of the analysis result by the CPU 301a will now be described with reference to FIG. 18.

Figure 19:
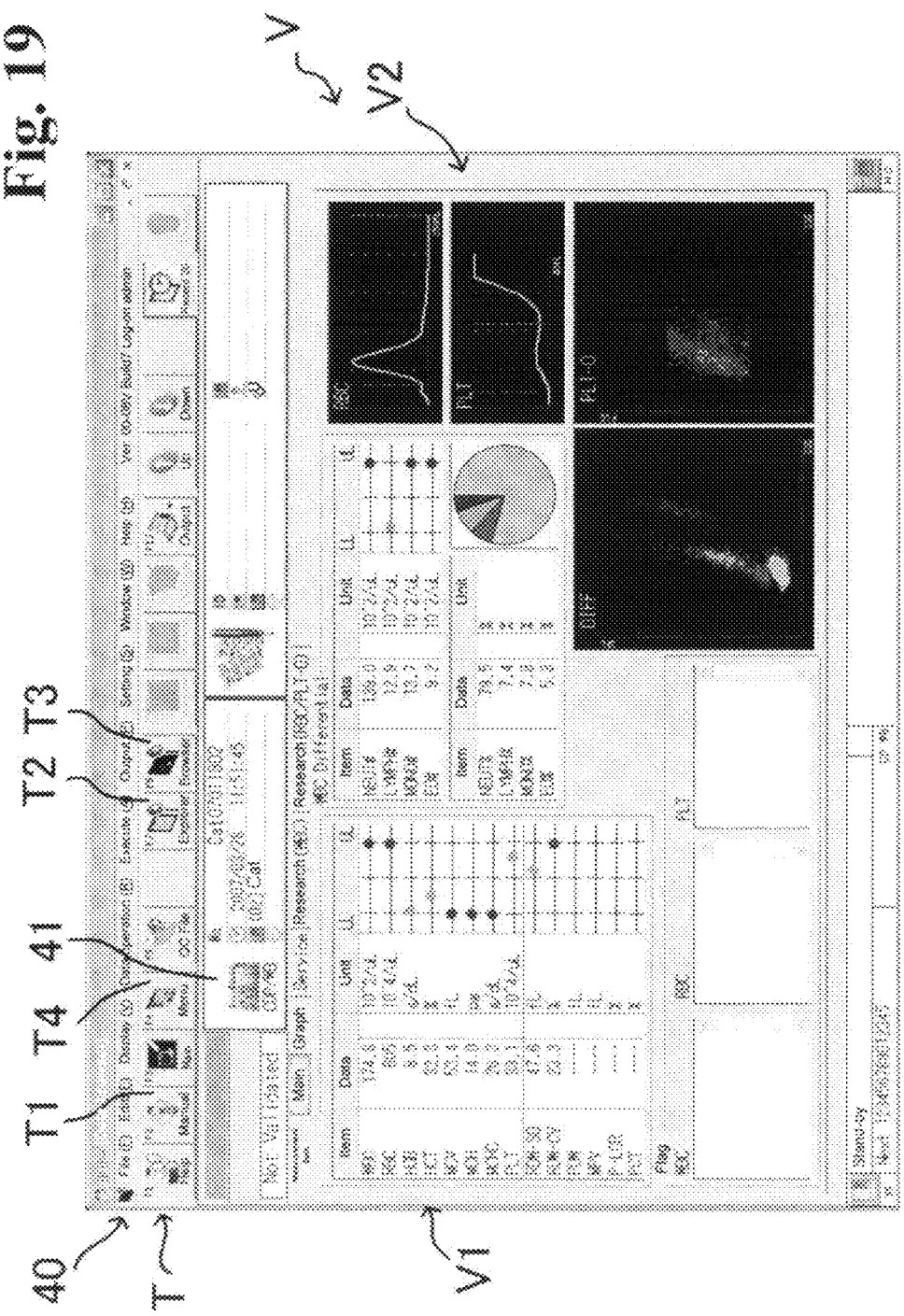
FIG. 19 is a view showing an analysis result display screen.

First, the CPU 301a reads out the analysis result stored in the hard disc 301d to the RAM 301c, and displays an analysis result screen shown in FIG. 19 on the display 302 through the image output interface 301h (step S901). A menu bar 40, the tool bar T, a specimen information region 41, the view V, and the like are arranged in the analysis result screen shown in FIG. 19. Furthermore, a measurement item display region V1 and a distribution map display region V2 are arranged in the view V, where the number of white blood cells, the number of red blood cells, and the like acquired by the CPU 301a are displayed on the measurement item display region V1, and the RBC histogram, the PLT histogram, the DIFF scattergram, and the PLT-O scattergram created by the CPU 301a are displayed on the distribution map display region V2. As shown in the specimen information region 41 of FIG. 19, a case of displaying the analysis result obtained by analyzing the measurement data of the blood of the cat will be described below.

Figure 20:
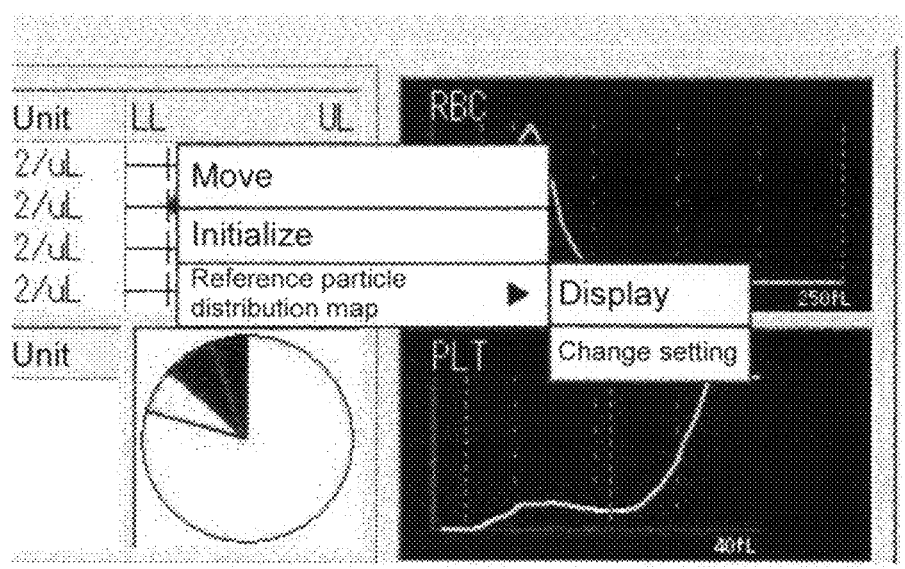
FIG. 20 is a view showing a right-click menu displayed when right clicked on the particle distribution map of the analysis result display screen shown in FIG. 19.

The CPU 301a then determines whether or not right-click is made on one of the particle distribution maps of the distribution map display region V2 (step S902), and displays the right-click menu on the display 302 as shown in FIG. 20 through the image output interface 301h if right-click is made on one of the particle distribution maps (step S903). If right-click is not made on either of the particle distribution maps, the CPU 301*a* proceeds to the process of step S913. Information indicating on which particle distribution map the right-click was made is stored in the RAM 301*c*. A case where the right-click is made on the DIFF scattergram of the distribution map region V2 will be described below.

After displaying the right-click menu in the process of step S903, the CPU 301*a* determines whether or not "reference particle distribution map" command arranged on the right-click menu is clicked (S904), where if the "reference particle distribution map" command is clicked, a hierarchical menu arranged with "display" command and "change setting" command is displayed on the display 302 through the image output interface 301*h* (step S905), as shown in FIG. 20. If the "reference particle distribution map" command of the right-click menu is not clicked, the CPU 301*a* proceeds to the process of step S913.

After displaying the hierarchical menu shown in FIG. 20, the CPU 301*a* determines which of the "display" command or the "change setting" command of the hierarchical menu is clicked (step S906), where if the "display" command is clicked, a predetermined reference particle distribution map is read out from the hard disc 301*d* to the RAM 301*c* (step S907), and the read-out reference particle distribution map is displayed on the display 302 with a predetermined displaying method through the image output interface 301*h* (step S908). The reference particle distribution map referred to herein is the particle distribution map registered by the user as the reference particle distribution map of the particle distribution maps of other specimens measured in the past in step S914 of FIG. 18 and in step S116 of FIG. 27 to be hereinafter described. The predetermined reference particle distribution displayed on the display 302 in step S908 and the predetermined displaying method of displaying the relevant reference particle distribution map are set in advance as default.

Figure 21:
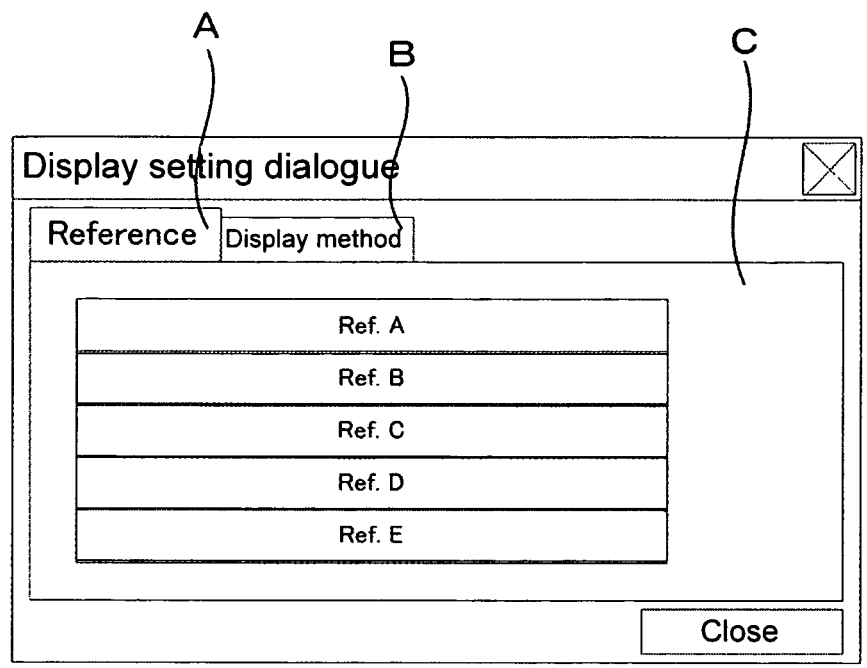
FIGS. 21 and 22 are views showing a display setting dialogue.
Figure 22:
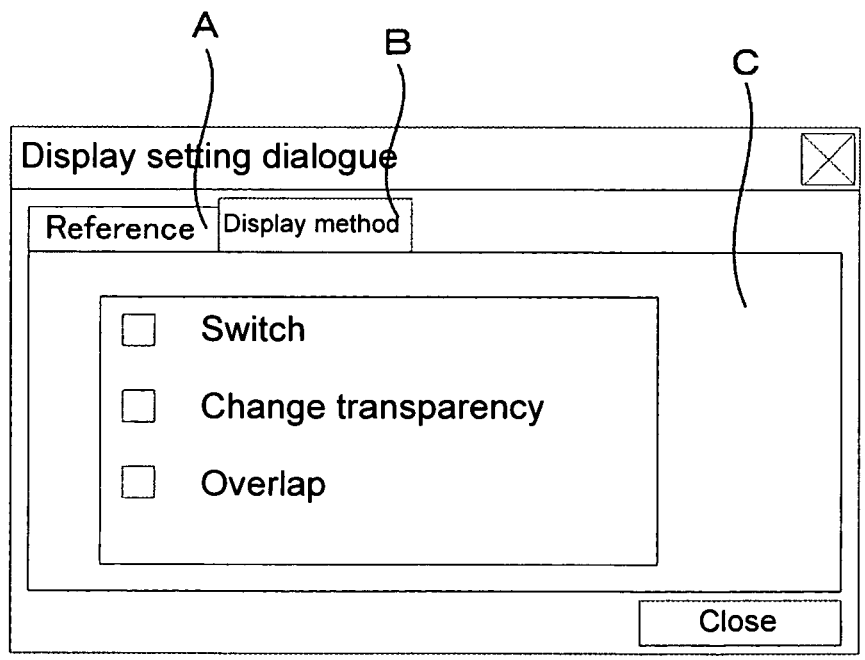

If the "change setting" command is clicked in step S906, the CPU 301*a* displays a display setting dialogue shown in FIGS. 21 and 22 for changing the display setting of the reference particle distribution map on the display 302 (step S909). As described above, the reference particle distribution map displayed in step S908 and the method of displaying the same are set in advance as default, but the user can change the display setting of the reference particle distribution map by default only with respect to the display process of the present time using the display setting dialogue. As shown in FIGS. 21 and 22, the display setting dialogue includes "reference" tab A, "displaying method" tab B, and a display region C for displaying the setting content. As shown in FIG. 21, when the "reference" tab A is selected, a plurality of reference particle distribution maps corresponding to the animal species of the measured specimen and the type of particle distribution map right clicked in the distribution map display region V2 of the plurality of reference particle distribution maps stored in the hard disc 301*d* is list displayed on the display region C. A plurality of reference particle distribution maps corresponding to the DIFF scattergram of the blood of the cat is list displayed on the display region C shown in FIG. 21. The user can set the reference particle distribution map to be displayed on the display 302 by selecting one of the reference particle distribution maps from the list displayed reference particle distribution maps. If the "displaying method" tab B is selected in the display setting dialogue, each item ("switch", "change transparency", and "overlap") of the displaying method of the reference particle distribution map, and the check box corresponding to each item are displayed on the display region C, as shown in FIG. 22. The user clicks one check box to select the displaying method of the reference particle distribution map. The displaying methods will be hereinafter described in detail.

After displaying the display setting dialogue in step S909, the CPU 301*a* determines whether or not change instruction of the display setting of the reference particle distribution map is accepted in the display setting dialogue (step S910), and changes the display setting of the reference particle distribution map when the change instruction of the display setting is accepted (step S911). If the change of the display setting is not accepted, the CPU 301*a* proceeds to the process of step S913.

After changing the display setting of the reference particle distribution map in step S911, the CPU 301*a* reads out the reference particle distribution map from the hard disc 301*d* based on the changed display setting (step S912), and displays the read-out reference particle distribution map on the display 302 (step S908).

Figure 23:
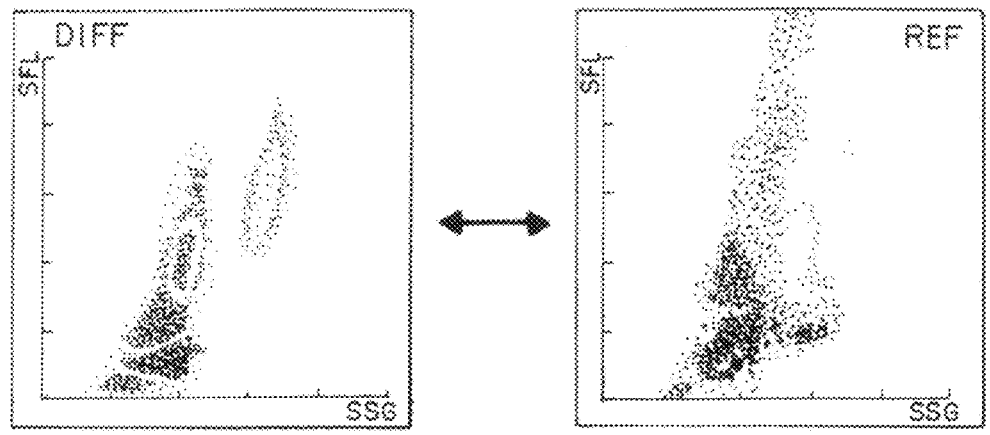
FIG. 23 is a view for describing a displaying method (switch display) of the reference particle distribution map.

In this case, if "switch" is set as the displaying method of the reference particle distribution map, the DIFF scattergram of the measured specimen and the reference DIFF scattergram are automatically alternately switched and displayed (view displayed with "Ref." character is reference DIFF scattergram) for every predetermined time (about every one second in the present embodiment), as shown in FIG. 23, on the display position of the DIFF scattergram on the analysis result screen shown in FIG. 19. More specifically, the reference DIFF scattergram is displayed at a position same as the position where the DIFF scattergram of the measured specimen is displayed at the same time as when the DIFF scattergram of the measured specimen displayed on the analysis result screen temporarily disappears from the screen. After about one second, the DIFF scattergram of the measured specimen is displayed at a position same as the position where the reference DIFF scattergram is displayed at the same time as when the reference DIFF scattergram disappears from the screen. Again after about one second, the reference DIFF scattergram is displayed at the same time as when the DIFF scattergram of the measured specimen disappears from the screen. Such processes are automatically repeated, so that two DIFF scattergrams are alternately switched and displayed on the same display position. The user can readily compare both particle distribution maps by alternately switching and displaying the particle distribution map of the measured specimen and the reference particle distribution map. Therefore, when the particle distribution map of a normal blood, for example, is displayed as the reference particle distribution map, evaluation of whether or not the measured specimen is abnormal can be carried out in one glance with the displayed reference particle distribution map as an index. Compared to a case of simply displaying the two particle distribution maps side by side, the difference in the distribution state of the particles in the two particle distribution maps can be readily understood by alternately switching and displaying the particle distribution map of the measured specimen and the reference particle distribution map at the same display position. The distribution of particles in the scattergram has coarse and dense portions depending on the blood sample, and slight difference of the distribution of the particles on the scattergram can be readily understood by alternately switching and displaying the scattergrams. Compared to a case of displaying the two particle distribution maps side by side, the display area for displaying the two particle distribution maps can be reduced. Thus, great amount of information related to the analysis result can be displayed on the analysis result screen. Since the switching operation is automatically performed, the trouble for the user to perform the switching operation is omitted. Furthermore, the character "Ref." is displayed for the reference particle distribution map, and thus the particle distribution map of the measured specimen and the reference particle distribution map can be readily distinguished.

A case in which "change transparency" and "overlap" is set for the displaying method of the reference particle distribution map will now be described. For the sake of convenience of the explanation, a case of displaying the reference particle distribution map corresponding to the RBC histogram of the blood of the cat will be described herein.

Figure 24:
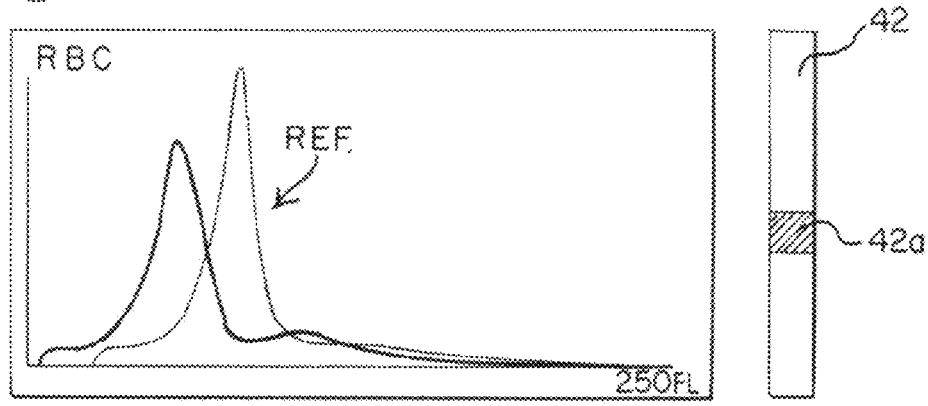
FIG. 24 is a view for describing a displaying method (change transparency) of the reference particle distribution map.

If "change transparency" is set for the displaying method of the reference particle distribution map, the RBC histogram of the measured specimen and the reference RBC histogram (denoted with "Ref." character) are overlapped and displayed, and the control bar 42 is displayed on the right side, as shown in FIG. 24. The control bar 42 has a function of changing the transparency of the distribution curve in the reference RBC histogram, where the transparency of the distribution curve of the reference RBC histogram is 100% and the distribution curve thereof is not displayed when the handle 42a of the control bar 42 is positioned at the very bottom of the control bar 42. The user drags the handle 42a upward, so that the transparency of the distribution curve of the reference RBC histogram becomes lower and the distribution curve thereof is gradually displayed. The user drags the handle 42a downward, so that the transparency of the distribution curve of the reference RBC histogram becomes higher and the distribution curve thereof is gradually disappeared. Both particle distribution maps can be readily compared by such displaying method. Compared to a case of displaying the two particle distribution maps side by side, the display area for displaying the two particle distribution maps is reduced. Thus, greater amount of information related to the analysis result can be displayed on the analysis result screen.

Figure 25:
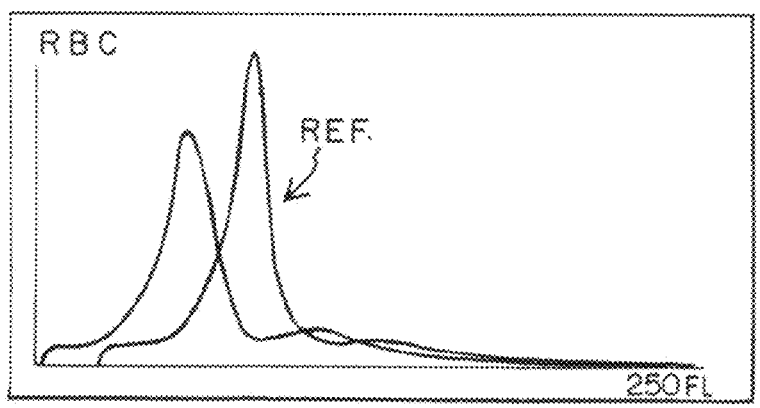
FIG. 25 is a view for describing a displaying method (overlap) of the reference particle distribution map.

If "overlap" is set for the displaying method of the reference particle distribution map, the RBC histogram of the measured specimen and the reference RBC histogram are overlapped and displayed, as shown in FIG. 25. In this case, the distribution curves in both RBC histograms are drawn and displayed with different colors from each other. Thus, both particle distribution maps can be readily compared. Compared to a case of displaying the two particle distribution maps side by side, the display area for displaying the two particle distribution maps can be reduced even when displaying the reference particle distribution map in "overlap". Thus, greater amount of information related to the analysis result can be displayed on the analysis result screen.

After displaying the reference particle distribution map in step S908, the CPU 301a determines whether or not the registration instruction of the reference particle distribution map is made (step S913). Specifically, as shown in FIG. 26, when "execute (A)" button arranged on the menu bar 40 of the analysis result screen is clicked, the menu including "register reference distribution map (R)" command is displayed, where when the "register reference distribution map (R)" command is selected, a hierarchical menu including commands indicating the type of particle distribution map ("RBC", "PLT", "DIFF", "PLT-O") is displayed. If one of the commands indicating the type of particle distribution map is clicked, the CPU 301a determines that registration instruction of the reference particle distribution map is made. If the registration instruction of the reference particle distribution map is not made, the CPU 301a returns the process. A case in which "PLT-O" command of the hierarchical menu shown in FIG. 26 is clicked will be described below.

If the registration instruction of the reference particle distribution map is made, the CPU 301a executes the registration process of the reference particle distribution map (step S914). In the registration process of step S914, the CPU 301a stores the PLT-O scattergram displayed on the distribution map display region V2 of the analysis result screen in the hard disc 301d as the reference particle distribution map corresponding to the PLT-O scattergram of the blood of the cat. In this case, "Ref. K", "Ref. 6" and the like are input as the file name corresponding to the particle distribution map to be stored, and the file name, the measurement date and time, and the specimen number are stored in the hard disc 301d in correspondence to the data of the particle distribution map along with the data of the particle distribution map. After the registration process of the reference particle distribution map is terminated, the CPU 301a returns the process.

The CPU 301a then determines whether or not instruction is made to display on the display 302 for the specimen (stored specimen) which analysis is completed in the past and the analysis result is stored in the hard disc 301d (step S3-10). Specifically, the CPU 301a determines whether or not "explorer" button T2 (see FIG. 19) arranged on the tool bar T of the analysis result screen is clicked. If the "explorer" button T2 is clicked, the CPU 301a executes the display process on the stored specimen (step S3-11). If the "explorer" button T2 is not clicked, the CPU 301a proceeds the process of step S3-12.

The display process of the stored specimen in step S3-11 will be described with reference to FIG. 27. First, the CPU 301a displays an explorer screen shown in FIG. 28, which is a list screen of the stored specimen, on the display 302 (step S111). As shown in FIG. 28, a plurality of specimens identified by animal species, specimen number, and the like are list displayed on the explorer screen.

The CPU 301a then determines whether or not selection of a specimen is accepted from the list displayed on the explorer screen (step S112). Specifically, if one of the specimens in the list is double clicked or if one of the specimens is selected by clicking and the "browser" button T3 (see FIG. 28) is clicked by the user, the CPU 301a determines that the selection of the specimen is accepted from the list.

Figure 29:
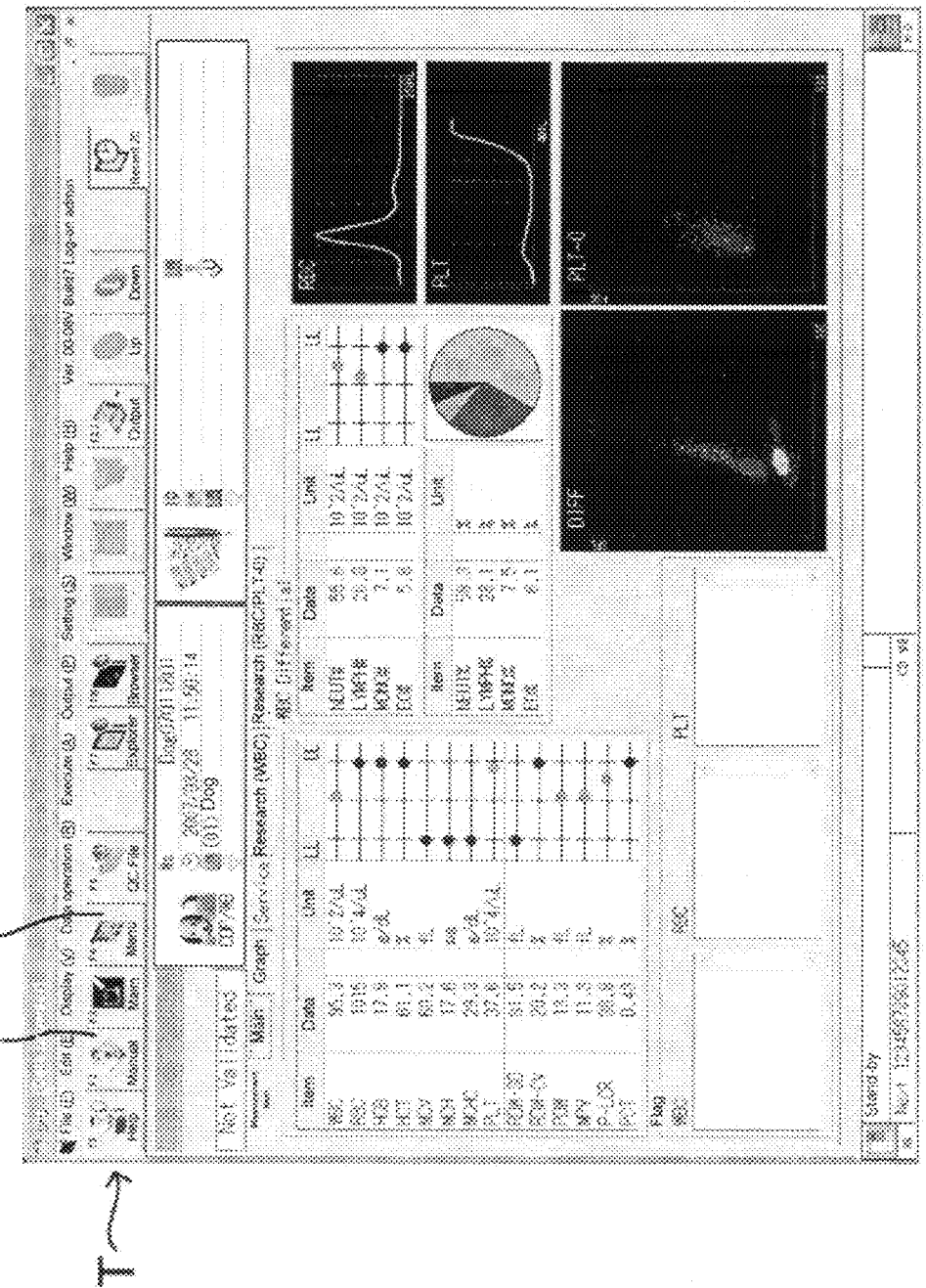
FIG. 29 is a view showing an analysis result display screen of the stored specimen.

If the selection of the specimen is accepted in step S112, the CPU 301a reads out the analysis result of the selected specimen from the hard disc 301d to the RAM 301c (step S113), and displays the read-out analysis result on the display 302 through the image output interface 301h (step S114). One example thereof is shown in FIG. 29. If the selection of the specimen is not accepted in step S112, the CPU 301a returns the process.

After the analysis result of the stored specimen is displayed on the display 302 in step S14, the CPU 301a determines whether or not registration instruction of the reference particle distribution map is made (step S115), and registers the particle distribution map displayed in the distribution map display region V2 as the reference particle distribution map if the registration instruction of the reference particle distribution map is made (step S116). The processes of step S115 and step S116 are the same as the processes of step S913 and step S914 described above, and thus the description thereof will be omitted. After the process in step S116 is terminated, the CPU 301a returns the process. Thus, in the present embodiment, the particle distribution map of the specimen which analysis is completed in the past can be registered as the reference particle distribution map of another specimen. Therefore, various particle distribution maps can be registered as the reference particle distribution map according to the need of the user.

The CPU 301a then determines whether or not a shutdown instruction is made by the user, specifically, whether or not "shutdown" icon S of the menu screen (see FIG. 12) is double clicked (step S3-12), and transmits a shutdown signal to the controller 8 through the communication interface 301g and the communicating section 9 of the measurement unit 2 if the "shutdown" icon S is double clicked (step S3-13). The menu screen shown in FIG. 12 is displayed if the "menu" button T4 of the tool bar T of the analysis result screen shown in FIGS. 19, 28, and 29 is clicked.

If the shutdown instruction is not made by the user, the CPU 301a returns to the process of step S3-3.

The controller 8 of the measurement unit 2 determines whether or not the shutdown signal is received from the CPU 301a of the data processing unit 3 (step S2-6), and executes the shutdown of the measurement unit 2 if the shutdown signal is received (step S2-7). The controller 8 returns to the process of step S2-2 if the shutdown signal is not received from the CPU 301a.

Therefore, according to the blood analyzer 1 of the present embodiment, the particle distribution map of the measured blood sample and the reference particle distribution map can be displayed so as to be compared without reducing the display area for displaying the analysis result information other than the particle distribution map.

According to the blood analyzer 1 of the present embodiment, the particle distribution map of the blood collected from a healthy subject may be displayed as the reference particle distribution map, or the particle distribution map of the blood collected from a subject having a predefined illness may be displayed. Thus, evaluation on whether or not the measured blood is collected from a health subject, evaluation on whether or not the measured blood is collected from a subject having a predefined illness, and the like can be easily made with reference to the displayed reference particle distribution map.

According to the blood analyzer 1 of the present embodiment, the particle distribution map of the specimen measured in the past can be freely registered as the reference particle distribution map. Therefore, if for example, the particle distribution map of the blood of the subjected measured one week before is registered as the reference particle distribution map, the particle distribution map obtained one week before can be displayed as the reference particle distribution map when measuring the blood collected from the same subject one week after and displaying the analysis result thereof. Thus, temporal change in the analysis result of the blood of the same subject can be checked.

According to the blood analyzer 1 of the present embodiment, the reference particle distribution map can be displayed for comparison with the particle distribution map of the measured blood even when analyzing blood of an animal species other than human being. Thus, even when measuring the blood of the animal species other than human being, the user can easily make an evaluation on whether or not the relevant blood is normal or abnormal, and the like by simply looking at the particle distribution map of the measured blood once.

In the above embodiment, an example of a blood analyzer for analyzing the blood of animals other than human being such as dogs and cats has been described by way of example, but the present invention is not limited thereto, and may applied to a blood analyzer for analyzing the blood of a human.

Furthermore, in the present embodiment, an example of a blood analyzer for analyzing the blood sample has been described, but the present invention is not limited thereto, and may be applied to a sample analyzer for analyzing a sample including biological particles such as urine cells other than the blood cells, fine ceramics particles, pigments, powder particles such as cosmetic powder, and the like.

In the present embodiment, the two-dimensional scattergram drawn using the side scattered light intensity in the X-axis direction and the side fluorescent light intensity or the forward scattered light intensity in the Y-axis direction is displayed, but the present invention is not limited thereto, and a three-dimensional scattergram taking the number of blood cells in the Z-axis direction may be displayed.

In the present embodiment, an example in which the display setting of the reference particle distribution map is made as a default, and the display setting of the reference particle distribution map by default is changed in the display setting dialogue displayed when right clicked on the particle distribution map of the analysis result screen is described, but the present invention is not limited thereto, and an operation of changing the display setting of the reference particle distribution map may be performed by clicking the "setting (S)" button arranged on the menu bar 40 of the analysis result screen.

In the present embodiment, an example in which the reference particle distribution map is displayed by the display setting of default of before change is made by the user in the next display process even if the display setting of the reference particle distribution map by default is changed by the user in the display setting dialogue is described, but the present inventions is not limited thereto, and the display of the reference particle distribution map may be carried out based on the display setting changed by the user even in the next display process when the display setting of the reference particle distribution map by default is changed by the user in the display setting dialogue.

In the present embodiment, the reference particle distribution map to be displayed on the display 302 and the displaying method thereof are set in advance at default, but the present invention is not limited thereto, and only the reference particle distribution map to be displayed on the display 302 may be set at default, and the displaying method may be set by the user every time the reference particle distribution map is displayed.

In the present embodiment, an example in which the reference particle distribution map is displayed on the display 302 based on the display setting by default if the display setting of the reference particle distribution map is not changed in the display setting dialogue is described, but the display setting by default may be customized by the user.

In the present embodiment, the change of the switching speed of the particle distribution map cannot be made when the displaying method of the reference particle distribution map is set to "switch", but the data processing unit 3 may be configured such that the switch speed of the particle distribution map can be changed. According to such configuration, the convenience of the user can be enhanced.

In the present embodiment, the switching operation of the particle distribution map is automatically performed when the displaying method of the reference particle distribution map is set to "switch", but the present invention is not limited thereto, and the switching operation of the particle distribution map may be made every time the user double clicks on the particle distribution map.

In the present embodiment, the particle distribution map of the measured specimen and one reference particle distribution map are alternately switched and displayed when the displaying method of the reference particle distribution map is set to "switch", but the present invention is not limited thereto, and the priority may be set from first to fifth, for example as the reference particle distribution map displayed on the display 302 of the reference particle distribution map stored in the hard disc 301d, and the first to the fifth reference particle distribution map may be sequentially and automatically switched and displayed. The first to the fifth reference particle distribution map may be sequentially switched and displayed every time the user double clicks on the particle distribution map.

In the present embodiment, two particle distribution maps are alternately switched and displayed by displaying the reference particle distribution map on the screen at the same time as when the particle distribution map of the measured blood sample disappears from the screen, but the present invention is not limited thereto, and display may be made such that the particle distribution map of the measured blood sample gradually switches to the reference particle distribution map using the morphing technique (technique of expressing a picture such that a certain image smoothly deforms into another image). In this case, the deformation of the particle distribution map by the morphing technique may be automatically carried out, or a control bar may be arranged and the particle distribution map may be deformed by having the user drag the handle of the control bar.

In the present embodiment, two particle distribution maps are alternately switched and displayed by displaying the reference particle distribution map on the screen at the same time as when the particle distribution map of the measured blood sample disappears from the screen, but the present invention is not limited thereto, and display may be made such that the reference particle distribution map gradually appears on the screen as the particle distribution map of the measured blood sample gradually disappears from the screen, and the particle distribution map of the measured blood sample gradually appears on the screen as the reference particle distribution map gradually disappears from the screen. Such switching may be automatically carried out, or a control bar may be arranged so that switching is carried out by having the user drag the handle of the control bar.

In the present embodiment, the RBC histogram and the DIFF scattergram are displayed on the distribution map display region V2 of the analysis result screen shown in FIG. 19, and the particle distribution map thereof and the reference particle distribution map are alternately switched and displayed, but the present invention is not limited thereto, and, for example, the blood sample of the same subject may be periodically measured, the analysis of the number of red blood cells, the DIFF scattergram and the like may be stored in the hard disc for every measurement, a graph showing temporal change of the number of red blood cells may be created, the created graph may be displayed on the analysis result screen, and the particle distribution map of the DIFF scattergram etc. acquired on the relevant date and time may be switched and displayed with the click operation every time an arbitrary point of the distribution curve shown on the graph is clicked by the mouse. Thus, not only the temporal change of the number of red blood cells can be understood, but the particle distribution map acquired on a certain date and time and the particle distribution map acquired on another date and time can be compared with a simple operation.

Furthermore, in the present embodiment, when the displaying method of the reference histogram is set to "change transparency", the transparency of the distribution curve of the reference histogram is changed by having the user drag the handle of the control bar, but the present invention is not limited thereto, and the transparency of the distribution curve may be automatically changed.

In the present embodiment, when the displaying method of the reference histogram is set as "change transparency", the transparency of the distribution curve of the reference histogram is changed, but the transparency of the distribution curve of the histogram of the measured blood sample may be changed. If the transparency of the distribution curve of the histogram of the measured blood sample becomes high, the transparency of the distribution curve of the reference histogram accordingly becomes lower, and if the transparency of the distribution curve of the measured blood sample becomes lower, the transparency of the distribution curve of the reference histogram accordingly becomes higher.

In the present embodiment, the reference histogram is displayed by "change transparency", but the not limited to the histogram, and the reference scattergram may be displayed by "change transparency".

Figure 30:
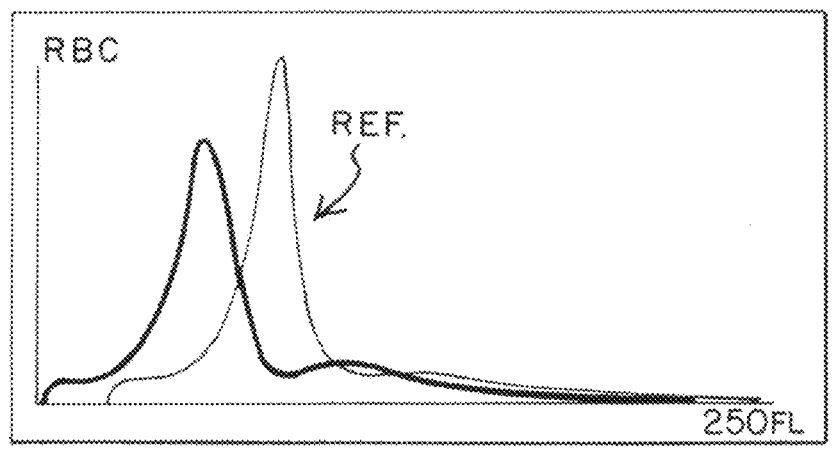
FIG. 30 is a view describing a variant of a displaying method of the reference particle distribution map.

In the present embodiment, the distribution curves of the two histograms are drawn with lines of the same thickness when displaying the histogram of the measured blood sample and the reference histogram in an overlapping manner, but the distribution curve in the histogram of the measured blood sample may be drawn thicker than the distribution curve of the reference histogram, as shown in FIG. 30. Thus, the two distribution curves are clearly distinguished. The two distribution curves may be distinguished by drawing the distribution curve of the reference histogram with a broken line.

Figure 18:
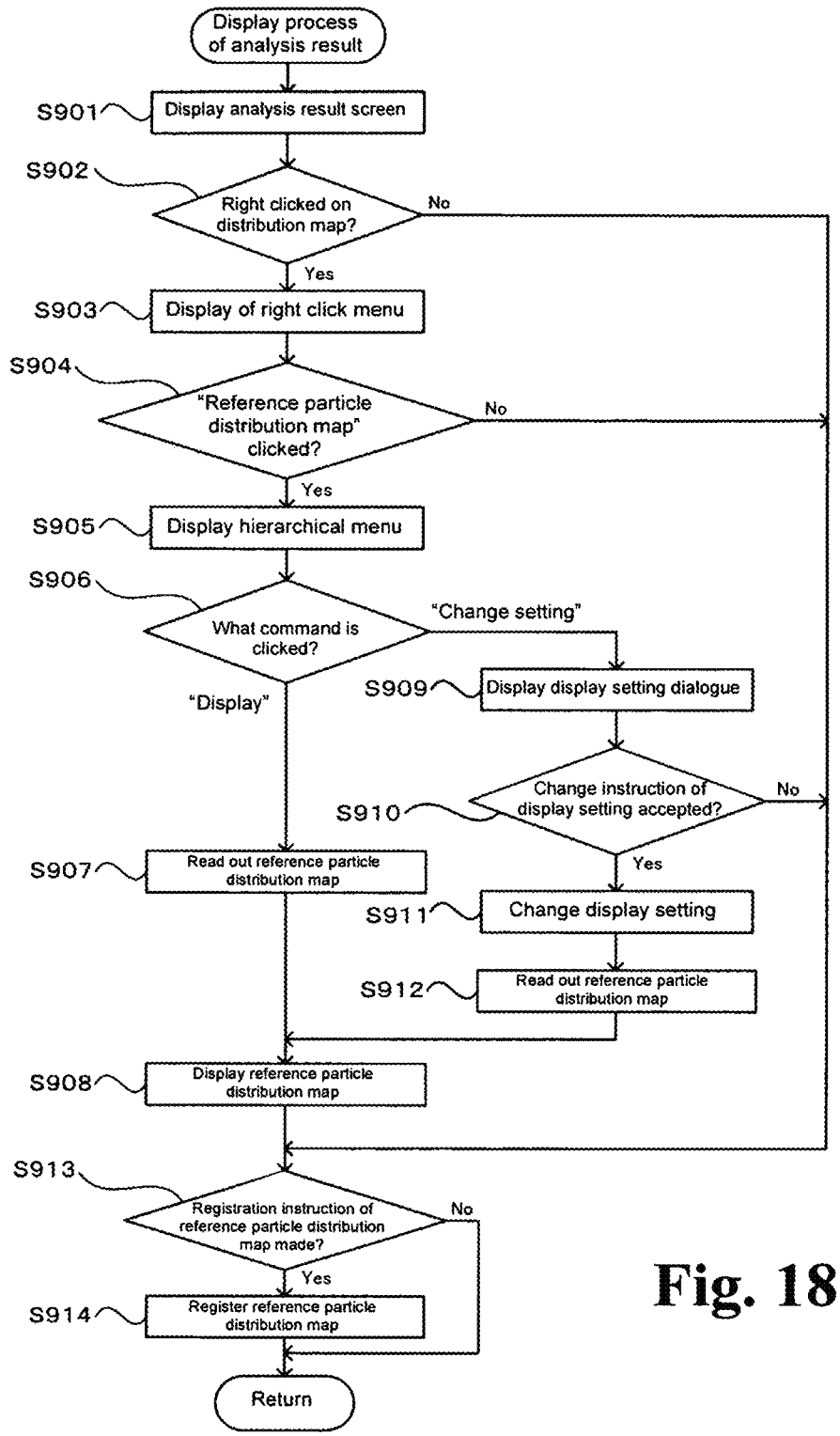
FIG. 18 is a flowchart showing a flow of display process of the analysis result.
Figure 27:
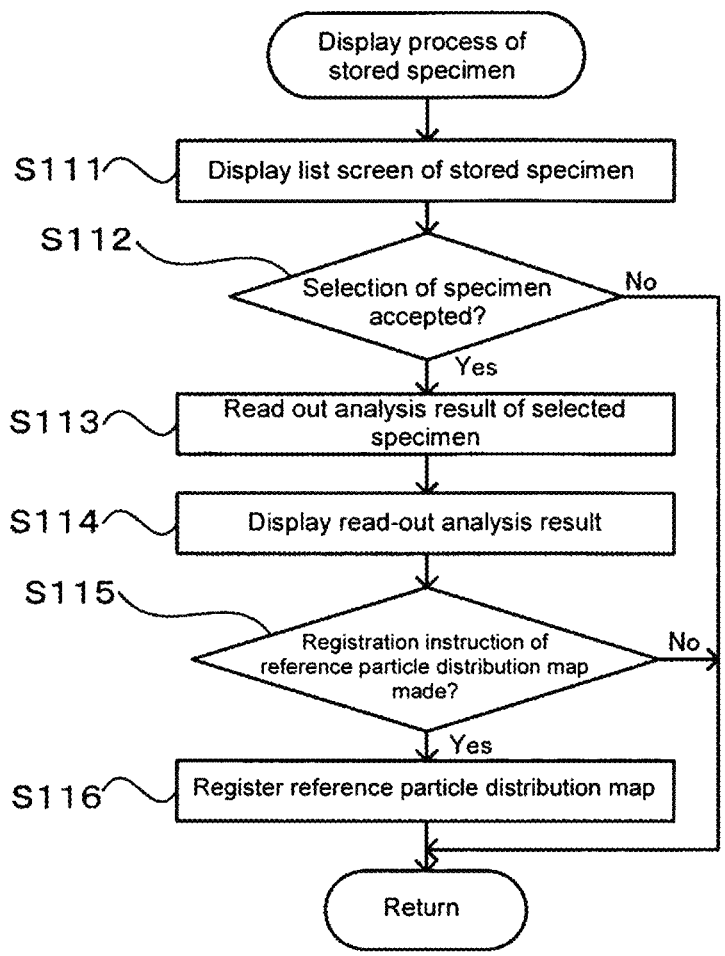
FIG. 27 is a view showing a flow of display process of an analysis result of a stored specimen.
Figure 28:
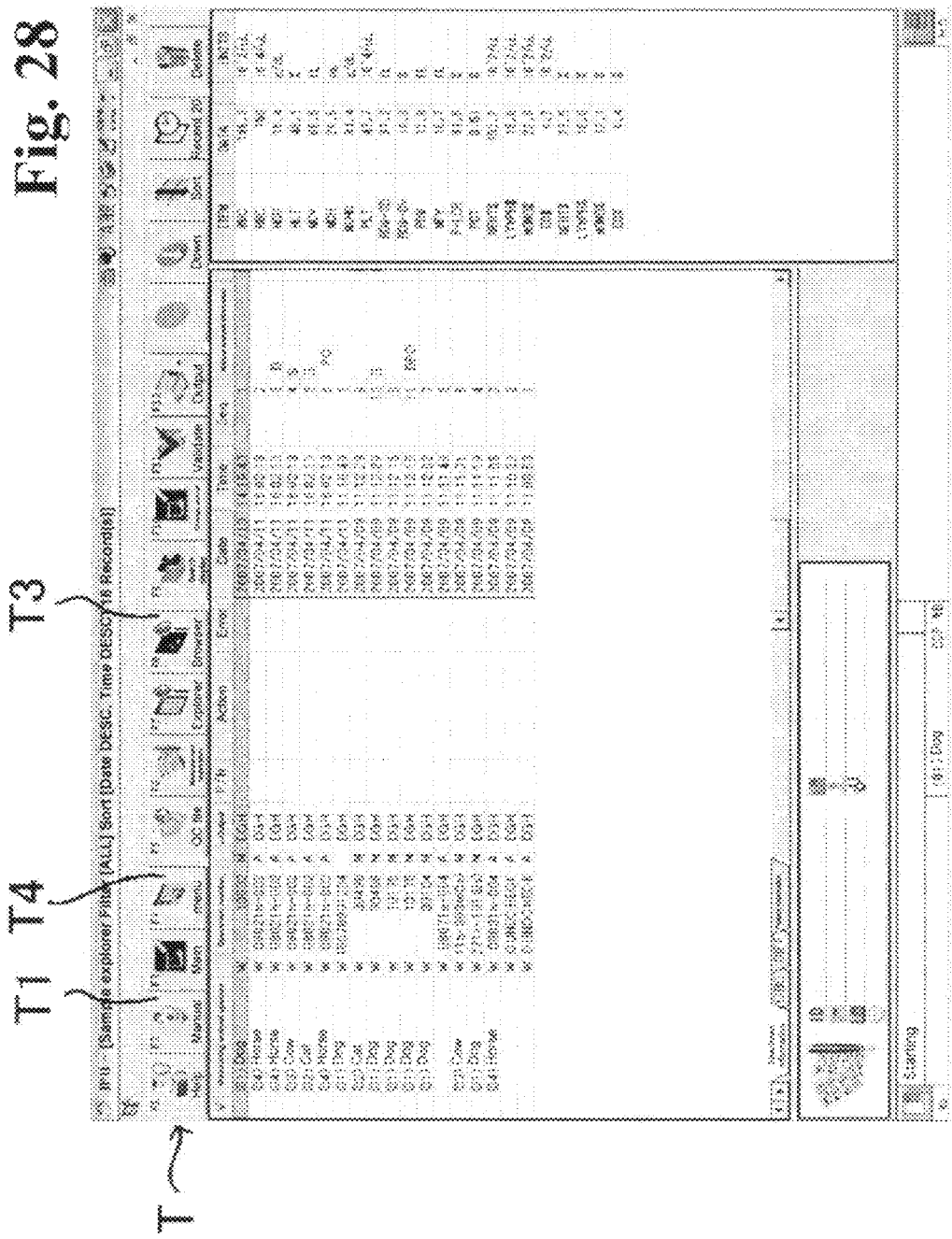
FIG. 28 is a view showing an explorer screen.

In the present embodiment, an example in which the reference particle distribution map is stored in the hard disc 301d of the data processing unit 3 by executing the registration process of the reference particle distribution map in step S914 of FIG. 18 and in step S116 of FIG. 27 is described, but the present invention is not limited thereto, and the reference distribution map may be read out from a portable recording medium such as CD-ROM storing the reference particle distribution map by means of the readout device 301e, the plurality of read-out particle distribution maps may be displayed on the display 302 through the image output interface 301h, the particle distribution map selected using a mouse etc. by the user from the displayed plurality of particle distribution maps may be accepted as a registration target, and the accepted particle distribution map may be stored in the hard disc 301d. The reference particle distribution map may be downloaded to the hard disc 301d through the communication network from an external equipment communicably connected to the data processing unit 3 through the communication network such as LAN or Internet.

In the present embodiment, the PLT-O scattergram obtained by measuring the blood of the cat is registered as the reference particle distribution map corresponding to the PLT-O scattergram of the blood of the cat in the registration process of the reference particle distribution map in step S914 of FIG. 18 and in step S116 of FIG. 27, but the present invention is not limited thereto, and the PLT-O scattergram obtained by measuring the blood of the cat may be registered as the reference particle distribution map corresponding to the PLT-O scattergram of the blood of the dog.

In the present embodiment, the reference particle distribution map stored in the hard disc 301d of the data processing unit 3 is displayed on the display 302, but the present invention is not limited thereto, and the reference particle distribution map may be read out from a portable recording medium such as CD-ROM storing the reference particle distribution map by means of the readout device 301e, and the read-out reference particle distribution map may be displayed on the display 302 without being stored in the hard disc 301d. The reference particle distribution map may be displayed on the display 302 through the communication network from an external equipment communicably connected to the data processing unit 3 through the communication network such as LAN or Internet.

In the present embodiment, the blood analyzer 1 is configured by the measurement unit 2 and the data processing unit 3, which is a separate body from the measurement unit 2, but may have the functions of both the measurement unit 2 and the data processing unit 3 loaded in a single device.

In the present embodiment, the input of the specimen number/selection of animal species are carried out using the mouse, the keyboard, and the like by the user on the screen displayed on the display 302 before the measurement of the specimen is started, but a barcode recorded with the animal species and the specimen number may be attached to the blood collecting tube, and the blood analyzer may be configured to read the barcode attached to the blood collecting tube with the barcode reader before measurement is started, for example.

In the present embodiment, the input of the specimen number/selection of animal species are carried out before the measurement of the specimen is started, but the present invention is not limited thereto, and the input of the specimen number/selection of animal species may be again carried out after the data processing of the measurement data is performed if the user makes an erroneous selection of the animal species. In this case, the data process of the measurement data is again performed preferably with the analysis condition corresponding to the subsequently selected animal species.

In the present embodiment, the particle distribution map of the measured blood sample and the reference particle distribution map are alternately switched and displayed in the same display region, but the particle distribution map of the measured blood sample and the reference particle distribution map may be displayed side by side. In such displaying method as well, the user can easily make an evaluation of whether or not the blood sample is normal or abnormal by simply looking at the particle distribution map of the measured blood sample once.

In the present embodiment, the particle distribution map having a horizontal axis and a vertical axis is used as the reference particle distribution map, but only the portion excluding the horizontal axis and the vertical axis may be used as the reference particle distribution map. Thus, when alternately switching the particle distribution map of the measured blood sample and the reference particle distribution map, the horizontal axis and the vertical axis are displayed on the screen and only the portion excluding the horizontal axis and the vertical axis may be alternately switched. When gradually deforming the particle distribution map of the measured blood sample to the reference particle distribution map using the morphing technique and the like, the horizontal axis and the vertical axis may be displayed on the screen, and only the portion excluding the horizontal axis and the vertical axis may be deformed.

What is claimed is:

1. A sample analyzer for analyzing a sample containing particles, comprising:
    a display;
    a measurement section for measuring a sample containing particles, wherein the sample corresponds to an animal other than human; and
    a data processing unit in communication with the display and the measurement section, the data processing unit being configured to:
    1) generate a sample particle distribution map representing a distribution of the particles contained in the sample, based on measurement data obtained by the measurement section; and
    2) control the display so as to alternately display the sample particle distribution map and a reference particle distribution map selected from among a plurality of sets of reference particle distribution maps corresponding to a species of the animal, at the predetermined display position, and morph the display to visually compare the distribution maps,
    wherein the data processing unit is configured to employ a plurality of different display methods to display the selected reference particle distribution map relative to the sample particle distribution map at the predetermined position;
    wherein the data processing unit comprises a memory, and is configured to store the sample particle distribution map in the memory as one of the reference particle distribution maps in the plurality of sets of reference particle distribution maps corresponding to the species of the animal that corresponds to the sample, according to a registration instruction.

2. The sample analyzer of claim 1, wherein when receiving a display instruction of the reference particle distribution map the data processing unit reads out the reference particle distribution map from the memory; and controls the display so as to display the reference particle distribution map at the predetermined display position.

3. The sample analyzer of claim 1, wherein the data processing unit automatically switches a display of the sample particle distribution map and a display of the reference particle distribution map.

4. The sample analyzer of claim 1, wherein the data processing unit switches a displayed information of the sample particle distribution map and a displayed information of the reference particle distribution map according to a switching instruction by a user.

5. The sample analyzer of claim 1, wherein according to one of the plurality of different display methods the data processing unit controls the display so that one of a first image of the sample particle distribution map and a second image of the reference particle distribution map are displayed at the predetermined display position gradually interchange by way of morphing, such that the first and second images deform into one another.

6. The sample analyzer of claim 5, wherein the data processing unit controls the display so that one of the first image of the sample particle distribution map and second image of the reference particle distribution map gradually appears at the predetermined display position as the other particle distribution map displayed at the predetermined display position gradually disappears from the predetermined display position.

7. The sample analyzer of claim 1, wherein according to one of the plurality of different display methods the data processing unit controls the display so as to display the reference particle distribution map on the sample particle distribution map at the predetermined display position distinguishably from the particle distribution map of the sample.

8. The sample analyzer of claim 1, wherein the data processing unit changes a display method of the reference particle distribution map according to a change instruction of the displaying method of the reference particle distribution map.

9. The sample analyzer of claim 1, wherein the reference particle distribution map comprises a particle distribution map generated by measuring a second sample different from the sample.

10. The sample analyzer of claim 9, wherein the reference particle distribution map is selected from a group consisting of a particle distribution map of a sample collected from a healthy living body, a particle distribution map of a sample collected from the living body with a predetermined illness, a particle distribution map of another sample collected from a living body from which the sample measured in the measurement section is collected, and a particle distribution map of a sample collected from a living body of an animal species different from that of the living body from which the sample measured in the measurement section is collected.

11. The sample analyzer of claim 1, wherein each of the sample particle distribution map and the reference particle distribution map comprises a scattergram generated using at least two types of characteristic information representing characteristics of particles in a sample comprising RBC/PLT and WBC.

12. The blood analyzer of claim 1, wherein the species of the animal comprises one of dog, cat, cow, or horse.

13. A sample analyzer for analyzing a sample containing particles, comprising:
a display;
a memory storing a plurality of sets of reference particle distribution maps corresponding to different animal species;
a measurement section for measuring a sample from an animal other than human containing particles;
generating means for generating a sample particle distribution map representing a distribution of the particles contained in the sample, based on measurement data obtained by the measurement section;
display controlling means for controlling the display so as to alternately display the sample particle distribution map at a predetermined display position and to display a reference particle distribution map from among a set of reference particle distribution maps corresponding to a species of the animal that corresponds to the sample at the predetermined display position and morph the display so as to visually compared the distribution maps, the set being selected from a plurality of sets of reference particle distribution maps corresponding to a plurality of different species of animal,
wherein the display controlling means employs a plurality of different display methods to display the reference particle distribution map relative to the particle distribution map at the predetermined position; and
storing means for storing a particle distribution map representing a distribution of particles contained in a first sample, generated by measuring the first sample, as one of the reference particle distribution maps in the set of reference particle distribution maps corresponding to the species of the animal that corresponds to the sample, according to a registration instruction.

14. A method for displaying a particle distribution map representing a distribution of particles contained in a sample from an animal other than human, comprising steps of:
(a) storing, in a memory, a plurality of sets of reference particle distribution maps corresponding to one or more animal species including a first sample particle distribution map representing a distribution of particles contained in a first sample, generated by measuring the first sample, as a reference particle distribution map among a set of reference particle distribution maps corresponding to a species of the animal that corresponds to the sample according to a registration instruction, the set being selected from a plurality of sets of reference particle distribution maps corresponding to a plurality of different species of animal;
(b) generating, using a computer processor, a second sample particle distribution map representing a distribution of particles contained in a second sample by measuring the second sample containing the particles and displaying the second particle distribution map at a predetermined display position; and
(c) alternately displaying the first sample particle distribution map stored in step (a) at the predetermined display position and morph the display so as to be visually compared with the second particle distribution map, wherein displaying comprises displaying the reference particle distribution map relative to the particle distribution map at the predetermined position according to a display method selected from among a plurality of display methods.

15. A blood analyzer for analyzing blood samples of a plurality of species of animals, comprising:
a display;
a measurement section for measuring a blood sample including both an RBC/PLT detecting section and a WBC detecting section configured to discriminate non-human blood cells; and
a data processing unit in communication with the display and the measurement section, the data processing unit being configured to
1) accept a selection of a non-human animal species to be measured among a plurality of non-human animal species;
2) generate a blood cell distribution map representing a distribution of blood cells contained in the blood sample, based on measurement data obtained by the measurement section; and
3) control the display so as to alternatingly display the blood cell distribution map of the blood sample and a reference blood cell distribution map selected from among a set of reference blood cell distribution maps corresponding to the selected animal species and morph the display so as to visually compare the distribution maps, the set being selected from a plurality of sets of reference blood cell distribution maps corresponding to a plurality of different species of animal,
wherein the data processing unit is configured to employ a plurality of different display methods to display the reference particle distribution map relative to the particle distribution map at the predetermined position
wherein the data processing unit comprises a memory, and is configured to store the blood cell distribution map of the blood sample in the memory as one of the reference blood cell distribution maps in the set of reference blood cell distribution maps corresponding to the selected animal species, according to a registration instruction.

16. The blood analyzer of claim 15, wherein
the data processing unit stores in the memory a plurality of reference blood cell distribution maps for every animal species, reads out the reference blood cell distribution map corresponding to the selected animal species from the memory according to a display instruction of the reference blood cell distribution map, and controls the display so as to display the read-out reference blood cell distribution map.

17. The blood analyzer of claim 15, wherein the data processing unit controls the display so as to display the blood cell distribution map of the blood sample on a predetermined distribution map display region, and display the reference blood cell distribution map on a reference distribution map display region adjacent to the predetermined distribution map display region.

18. A blood analyzer for analyzing blood samples of a plurality of species of animals, comprising:
   a display;
   a memory;
   a measurement section for measuring a blood sample including both an RBC/PLT detecting section and a WBC detecting section configured to discriminate non-human blood cells; and
   accepting means for accepting a selection of an animal species to be measured from among a plurality of animal species other than human;
   generating means for generating a blood cell distribution map representing a distribution of blood cells contained in the blood sample, based on measurement data obtained by the measurement section;
   display controlling means for controlling the display so as to alternatingly display the blood cell distribution map of the blood sample and a reference blood cell distribution map selected from among a set of reference blood cell distribution maps corresponding to the selected animal species and for morphing the display so as to visually compare the distribution maps, the set being selected from a plurality of sets of reference blood cell distribution maps corresponding to a plurality of different species of animal, wherein the display controlling means employs a plurality of different display methods to display the reference particle distribution map relative to the particle distribution map at the predetermined position; and
   storing means for storing the blood cell distribution map of the sample in the memory as one of the reference blood cell distribution maps in the set of reference blood cell distribution maps corresponding to the selected species of animal, according to a registration instruction.

19. A method for displaying a blood cell distribution map in a blood analyzer for analyzing blood samples of a plurality of species of animals, comprising steps of:
   a) selecting an animal species to be measured from among a plurality of non-human animal species;
   b) storing, in a memory, a blood cell distribution map representing a distribution of blood cells contained in a first sample generated by measuring the first sample, as a reference blood cell distribution map among a set of reference blood cell distribution maps corresponding to a species of the animal that corresponds to the sample according to a registration instruction, the set being selected from a plurality of sets of reference blood cell distribution maps corresponding to a plurality of different species of animal;
   c) generating, using a computer processor, a blood cell distribution map representing a distribution of blood cells contained in a second blood sample by measuring the second blood sample; and
   d) displaying the generated blood cell distribution map stored in step (b) and the reference blood cell distribution map corresponding to the animal species selected in step a) so as to be visually compared, wherein the displaying comprises displaying the reference particle distribution map relative to the particle distribution map at the predetermined position and morphing the display so as to visually compare the distribution maps according to a display method comprising one of:
   a first display method that comprises alternately displaying the particle distribution map of the sample and the reference particle distribution map at the predetermined display position;
   a second display method that comprises displaying so that one of the particle distribution map of the sample and the reference particle distribution map displayed at the predetermined display position gradually changes to the other particle distribution map; or
   a third display method that comprises displaying the reference particle distribution map on the particle distribution map of the sample at the predetermined display position distinguishably from the particle distribution map of the sample.

* * * * *